(12) United States Patent
Mustapha

(10) Patent No.: US 11,779,451 B2
(45) Date of Patent: Oct. 10, 2023

(54) PERIPHERAL VASCULAR FILTRATION SYSTEMS AND METHODS

(71) Applicant: Jihad A. Mustapha, Grandville, MI (US)

(72) Inventor: Jihad A. Mustapha, Grandville, MI (US)

( * ) Notice: Subject to any disclaimer, the term of this patent is extended or adjusted under 35 U.S.C. 154(b) by 357 days.

(21) Appl. No.: 17/074,285

(22) Filed: Oct. 19, 2020

(65) Prior Publication Data

US 2021/0030524 A1 Feb. 4, 2021

Related U.S. Application Data

(63) Continuation of application No. 16/014,712, filed on Jun. 21, 2018, now Pat. No. 10,842,609.

(Continued)

(51) Int. Cl.
*A61B 17/221* (2006.01)
*A61F 2/01* (2006.01)
(Continued)

(52) U.S. Cl.
CPC .............. *A61F 2/0108* (2020.05); *A61F 2/82* (2013.01); *A61F 2/011* (2020.05);
(Continued)

(58) Field of Classification Search
CPC ...... A61F 2/011; A61F 2/82; A61F 2002/016; A61F 2220/0025; A61F 2230/0067;
(Continued)

(56) References Cited

U.S. PATENT DOCUMENTS

| 6,245,012 B1 | 6/2001 | Kleshinski |
| 6,277,138 B1 | 8/2001 | Levinson et al. |

(Continued)

FOREIGN PATENT DOCUMENTS

| JP | 2003-220062 A | 8/2003 |
| JP | 2007-083089 A | 4/2007 |

(Continued)

OTHER PUBLICATIONS

Adient Medical; http://www.adientmedical.com/; Vascular Filter; company mission, technology and contact information; 1 page.

(Continued)

*Primary Examiner* — Kathleen S Holwerda
(74) *Attorney, Agent, or Firm* — Michele V. Frank; Venable LLP

(57) ABSTRACT

A peripheral vascular filter according to some aspects of the invention includes a filter body forming a cavity therein, the filter body having a proximal end and a distal end in a length-wise direction of the peripheral vascular filter, the filter body having an opening in the proximal end thereof; a spring system arranged proximal to the filter body and in mechanical connection with the filter body and with a filter wire, the spring system being stretchable along the length-wise direction; a plurality of retractor wires, each retractor wire having a distal end connected to the filter body, and a proximal end connected to spring system. In a deployed configuration, the spring system absorbs forces applied to the filter wire proximal to the filter body to prevent the peripheral vascular filter from becoming dislodged from a position in a peripheral vasculature.

17 Claims, 25 Drawing Sheets

Related U.S. Application Data

(60) Provisional application No. 62/524,217, filed on Jun. 23, 2017.

(51) Int. Cl.
*A61F 2/82* (2013.01)
*A61M 25/09* (2006.01)

(52) U.S. Cl.
CPC . *A61F 2002/016* (2013.01); *A61F 2210/0057* (2013.01); *A61F 2220/0025* (2013.01); *A61F 2230/008* (2013.01); *A61F 2230/0067* (2013.01); *A61F 2230/0069* (2013.01); *A61F 2230/0091* (2013.01); *A61F 2250/0017* (2013.01); *A61F 2250/0023* (2013.01); *A61M 25/09* (2013.01)

(58) Field of Classification Search
CPC ........ A61F 2230/0068; A61F 2230/008; A61F 2230/0091; A61M 25/09; A61B 17/221
See application file for complete search history.

(56) References Cited

U.S. PATENT DOCUMENTS

| | | | |
|---|---|---|---|
| 7,001,424 B2 | 2/2006 | Patel et al. | |
| 7,720,257 B2 | 5/2010 | Morellas | |
| 7,771,452 B2 | 8/2010 | Pal et al. | |
| 8,647,360 B2 | 2/2014 | Gilson et al. | |
| 8,814,925 B2 | 8/2014 | Hilaire et al. | |
| 2001/0007947 A1* | 7/2001 | Kanesaka | A61F 2/0105 606/198 |
| 2001/0020175 A1 | 9/2001 | Yassour et al. | |
| 2002/0007190 A1 | 1/2002 | Wulfman et al. | |
| 2002/0072730 A1 | 6/2002 | McGill et al. | |
| 2003/0009190 A1 | 1/2003 | Kletschka et al. | |
| 2003/0078614 A1* | 4/2003 | Salahieh | A61F 2/01 606/200 |
| 2004/0116960 A1 | 6/2004 | Demond et al. | |
| 2006/0015136 A1 | 1/2006 | Besselink | |
| 2007/0055365 A1 | 3/2007 | Greenberg et al. | |
| 2007/0129791 A1 | 6/2007 | Balaji | |
| 2007/0225748 A1 | 9/2007 | Park et al. | |
| 2008/0125806 A1 | 5/2008 | Mazzocchi et al. | |
| 2009/0105747 A1 | 4/2009 | Chanduszko et al. | |
| 2009/0240238 A1 | 9/2009 | Grodrian | |
| 2011/0022074 A1* | 1/2011 | Powell | A61F 2/01 606/200 |
| 2012/0071916 A1* | 3/2012 | Kusleika | A61M 25/09 606/200 |
| 2013/0226222 A1* | 8/2013 | Eggers | A61F 2/01 606/200 |
| 2014/0121672 A1* | 5/2014 | Folk | A61F 2/013 606/127 |
| 2014/0276922 A1* | 9/2014 | McLain | A61B 17/3207 606/127 |
| 2015/0150671 A1 | 6/2015 | Gilson et al. | |
| 2016/0151144 A1 | 6/2016 | Eggers | |
| 2016/0242893 A1 | 8/2016 | Joshi et al. | |

FOREIGN PATENT DOCUMENTS

| | | |
|---|---|---|
| JP | 2009-508657 A | 3/2009 |
| JP | 2012-502679 A | 2/2012 |
| WO | 1999022673 A1 | 5/1999 |
| WO | 2007/035885 A2 | 3/2007 |
| WO | 2010/029190 A1 | 3/2010 |
| WO | 2015/079401 A2 | 6/2015 |

OTHER PUBLICATIONS

International Search Report and Written Opinion dated Sep. 7, 2018 in corresponding International Application No. PCT/US2018/038771 (11 pages).
Office Action for corresponding U.S. Appl. No. 16/014,712 dated Feb. 4, 2020.
Final Office Action for corresponding U.S. Appl. No. 16/014,712 dated May 5, 2020.
Notice of Allowance for corresponding U.S. Appl. No. 16/014,712 dated Jul. 17, 2020.
Extended European Search Report dated May 20, 2021, directed to EP Application No. 18821522.2; 9 pages.
Examination report No. 1 for standard patent application dated Apr. 5, 2023, directed to Australian Patent Application Mo 2018290235; 4 pages.
Notification of Reason for Rejection dated Feb. 8, 2022, directed to JP Application No. 2020-520194; 7 pages.
Certified Decision of Rejection dated Sep. 7, 2022, directed to JP Application No. 2020-520194; 5 pages.
Notification of Reasons for Rejection dated Jun. 15, 2023, directed to JP Application No. 2022-080221; 5 pages.

* cited by examiner

PERIPHERAL VASCULAR FILTRATION SYSTEMS AND METHODS

CROSS-REFERENCE TO RELATED APPLICATIONS

This application is a continuation of U.S. patent application Ser. No. 16/014,712 filed on Jun. 21, 2018, now U.S. Pat. No. 10,842,609, which claims priority to U.S. Provisional Application No. 62/524,217 filed Jun. 23, 2017, the contents of which are hereby incorporated by reference in their entireties.

BACKGROUND

1. Technical Field

The field generally relates to a vascular filter, and more particularly to devices and methods for filtering bodily fluids in the peripheral vasculature.

2. Discussion of Related Art

Filtering devices have been used for years to capture blood clots in the vena cava and prevent them from migrating through the heart and into the lungs. A thrombus (blood clot) may break away from the vessel wall, and, depending on the size of the thrombus, may result in pulmonary embolism if it travels from the peripheral vasculature through the heart and into the lungs. Accordingly, a filter can be placed in the inferior vena cava, for example, to capture the thrombus before it moves into the heart.

Existing filtering devices are designed for use the in the vena cava, but are too large to be used in the peripheral vasculature, such as below the knee, for example. Further, many of the filtering systems use a guide wire to deploy and remove the filter. The filter is rigidly fixed to the guide wire, such that any movement of the guide wire results in movement of the filter. This can cause the filter to be inadvertently dislodged from its intended position. Finally, the devices are designed to trap clots once the filter has been deployed in the vasculature, but do not have a mechanism for maintaining the clots inside the filter during removal of the filter. Thus, captured clots can be re-introduced into the blood stream.

There remains an unmet need for effective and reliable filtration options for the peripheral vasculature.

SUMMARY

A peripheral vascular filter includes a filter body forming a cavity therein, the filter body having a proximal end and a distal end in a length-wise direction of the peripheral vascular filter, the filter body having an opening in the proximal end thereof; a spring system arranged proximal to the filter body and in mechanical connection with the filter body and with a filter wire, the spring system being stretchable along the length-wise direction; a plurality of retractor wires, each retractor wire having a distal end connected to the filter body, and a proximal end connected to spring system. In a deployed configuration, the spring system absorbs forces applied to the filter wire proximal to the filter body to prevent the peripheral vascular filter from becoming dislodged from a position in a peripheral vasculature.

According to one aspect, the filter body comprises a stent forming the opening in a proximal end thereof, and a cone-shaped filter connected to the stent to close a distal opening of the stent. According to one aspect, the spring system comprises a helical spring disposed between the retractor wires and the filter wire.

According to one aspect, the spring system comprises a flexible loop disposed at the proximal end of each of the plurality of retractor wires. According to one aspect, the flexible loop is configured to lengthen or contract to absorb forces applied to the filter wire proximal to the filter body to prevent the peripheral vascular filter from becoming dislodged.

According to one aspect, the filter body further includes a support ring at a proximal end of the filter body. According to one aspect, the filter body further includes a support ring at a distal end of the stent.

According to one aspect, the stent is a self-expanding stent. According to one aspect, in the deployed configuration, the filter body exerts an expansion force on a tissue lumen in which the filter body is disposed, creating a friction force that resists displacement of the filter body in the tissue lumen.

According to one aspect, the filter body comprises a cylindrical primary filter and a cone-shaped secondary filter attached to the primary filter. According to one aspect, the secondary filter is partially disposed inside a lumen formed by the primary filter. According to one aspect, the proximal end of the secondary filter is connected to an inner surface of primary filter.

According to one aspect, the peripheral vascular filter has a maximum diameter between about 2 mm and about 26 mm. According to one aspect, the peripheral vascular filter has a maximum diameter between about 2 mm and about 4 mm. According to one aspect, the filter body comprises a porous material having pores between about 5 μm and about 80 μm. According to one aspect, the pores of the filter body are larger at a proximal end of the filter body than at a distal end of the filter body.

According to one aspect, the peripheral vascular filter is adapted for use in a peripheral vasculature. According to one aspect, the plurality of retractor wires comprises three retractor wires. According to one aspect, the spring system has a maximum width that is less than 0.4 inches.

A method for filtering fluid in a peripheral vasculature includes deploying a filter in the peripheral vasculature, the filtering having a proximal opening through which fluid enters, and a spring system for absorbing forces that would cause the filter to become dislodged from a deployed position in the peripheral vasculature; capturing large particles suspended in the fluid in the filter; prior to retrieval, collapsing the proximal opening of the filter, thereby trapping the large particles within the filter; and removing the filter from the peripheral vasculature while the trapped large particles remain in the filter.

A peripheral vascular filter according to another aspect includes a filter body forming a cavity therein, the filter body having an opening in a proximal end thereof; a catheter adapted to form a helix concentric to the filter body, a distal end of the catheter being fixed to the filter body and a proximal end of the catheter extending proximal to the filter body; a plurality of expandable filter walls connected to the filter body adjacent to the opening; and a plurality of retractor wires, each retractor wire having a distal end connected to one of the plurality of expandable filter walls, and a proximal end connected to the catheter proximal to the filter body, wherein, in a deployed configuration, the plurality of expandable filter walls are compressed, and the opening in the proximal end of the filter body is unobstructed, and in a retrieval configuration, the expandable filter walls are expanded to obstruct the opening in the proximal end of the filter body.

According to one aspect, the filter body comprises a stent forming the opening in a proximal end thereof, and a cone-shaped filter connected to the stent to close a distal opening of the stent. According to one aspect, the expandable filter walls are expanded by a force applied to a proximal end of the catheter.

According to one aspect, the filter further includes a guide wire disposed inside the catheter, wherein the guide wire comprises a spring wire system, the spring wire system adapted to absorb forces exerted on the guide wire to prevent the peripheral vascular filter from becoming dislodged.

According to one aspect, the filter body comprises a porous material having pores between about 10 μm and about 80 μm. According to one aspect, the pores of the filter body are larger at a proximal end of the filter body than at a distal end of the filter body.

A peripheral vascular filter according to another aspect includes a catheter having a proximal end and a distal end, the distal end having a helical configuration; a self-expanding stent in mechanical connection with the catheter, the self-expanding stent forming a lumen, the catheter forming a helix along a surface of the self-expanding stent; a net forming a cone, the net having a proximal end in mechanical connection with the self-expanding stent, the net adapted to capture particles flowing through the lumen of the stent; a connector ring disposed around the catheter proximal to the mechanical connection with the stent; a plurality of retractor wires, each retractor wire connecting one of the plurality of expandable filter walls to the catheter at a position proximal to the stent, wherein, in a retrieval configuration, the support wires deploy the expandable filter walls to obstruct a proximal opening of the lumen formed by the self-expanding stent.

According to one aspect, the filter further includes a wire disposed in the lumen of the catheter, the wire having a spring portion in mechanical connection with the distal end of the catheter, the spring portion configured to absorb forces applied to the wire to prevent dislodgement of the peripheral vascular filter.

According to one aspect, a method for filtering fluid in a peripheral vasculature includes deploying a filter in the peripheral vasculature, the filtering having a proximal opening through which fluid enters; capturing large particles suspended in the fluid in the filter; prior to retrieval, obstructing the proximal opening of the filter, thereby trapping the large particles within the filter; and removing the filter from the peripheral vasculature while the trapped large particles remain in the filter.

BRIEF DESCRIPTION OF THE DRAWINGS

Further objectives and advantages will become apparent from a consideration of the description, drawings, and examples.

DETAILED DESCRIPTION

Figure 1:
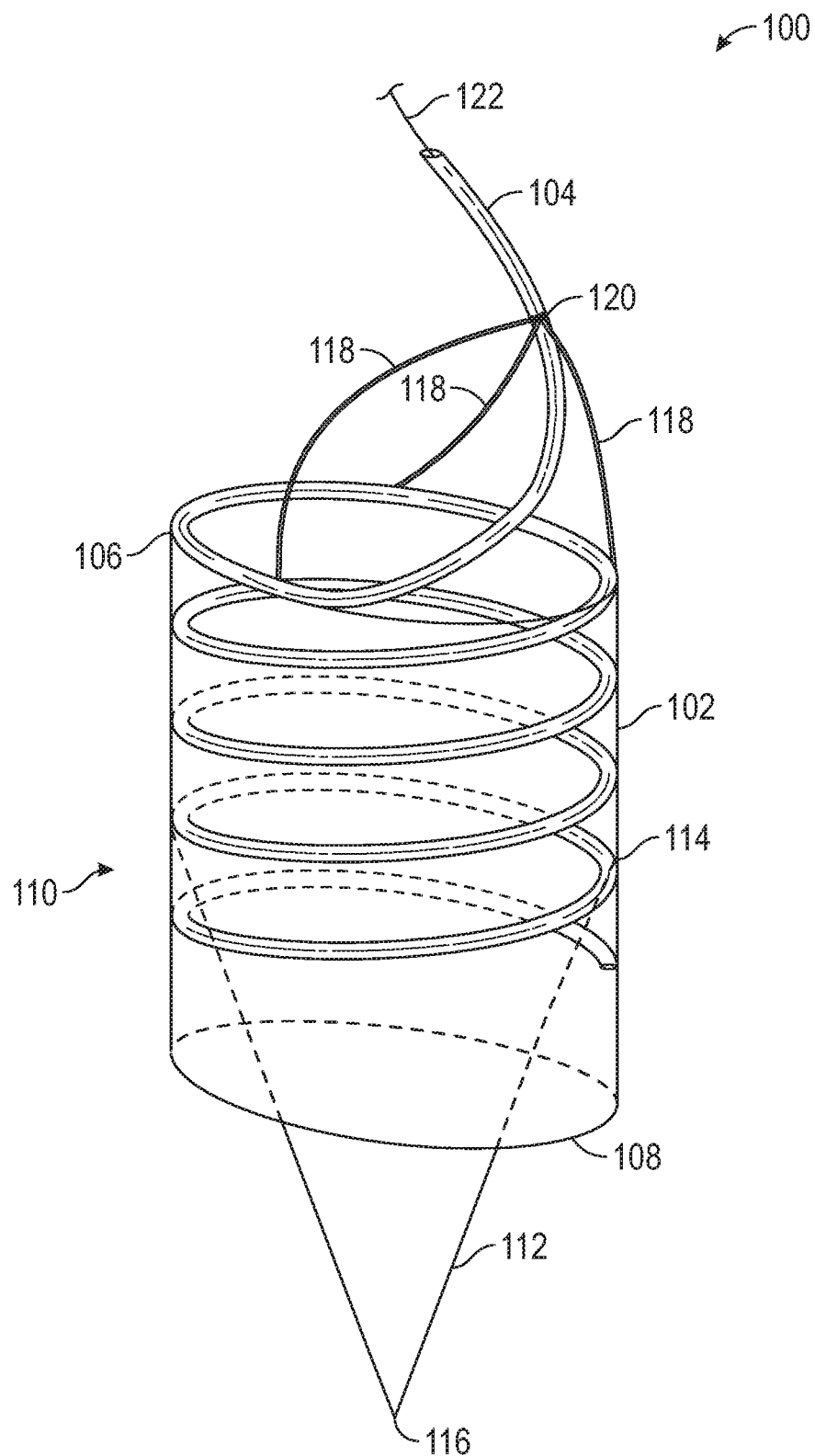
FIG. 1 shows a peripheral vascular filter in a deployed configuration.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The devices and methods contemplated are configured to reliably and effectively trap and remove blood clots in the vasculature, especially in the peripheral vasculature. The devices and methods in accordance with the principles of the invention are configured and adapted to be temporarily disposed in a vessel during interventional treatments, to prevent blood clots that become dislodged during the interventional treatments from traveling through the vasculature to the heart and lungs.

The device in one configuration has a filter body forming a cavity therein. The filter body has an opening in its proximal end. The terms "proximal" and "distal" are defined herein according to the direction of the fluid flowing through the cavity in which the filter is disposed. Proximal is intended to mean upstream, while distal is intended to mean downstream. Accordingly, fluid flowing through the cavity flows into the proximal opening of the filter body, and moves toward the distal end of the filter body. The direction of the fluid flowing through the cavity is parallel to the length-wise direction of the filter. Further, the aspects of the filter described with respect to one embodiment are not intended to be limited to that embodiment. Instead, those aspects may also be applied to other embodiments of the filter.

The filter body comprises a porous material. Particles that are larger than the pores of the filter body become trapped inside the filter body, while smaller particles exit the sides and distal end of the filter body through the pores. Fluid can therefore continue to flow through the filter, but larger particles such as blood clots in the fluid will be prevented from traveling downstream of the filter.

In one aspect, the filter includes a spring system. The spring system provides a connection between the filter and the guide wire that the operator uses to manipulate the filter from outside the patient's body. The operator deploys the filter in the patient's vasculature at a target position. While the filter is deployed, the filter remains tethered to the guide wire. If the guide wire is rigidly fixed to the filter, any inadvertent movement of the guide wire by the operator or by the patient can push or pull the filter away from the target position in the vasculature. This can not only change the location of the filter, but can also cause particles trapped in the filter to be re-released into the bloodstream.

The spring system can address this problem by absorbing forces applied to the guide wire. When forces are inadvertently applied to the guide wire, the spring system can expand, contract, or deform in a way that allows the system to absorb with forces, without transferring them to the filter. In one aspect, the filter body is self-expanding, such that it applies an outwardly radiating force on the wall of the vessel in which the filter is disposed. The outwardly radiating force creates a frictional force that resists motion of the filter with respect to the vessel wall. Thus, when forces are inadvertently applied to the guide wire, the spring system absorbs the forces without translating them to the filter, and the filter maintains its position in the peripheral vasculature due to the friction forces between the filter body and the vessel wall.

In one aspect, the spring system is a system that connects the filter body to the guide wire. The spring system may instead be incorporated into the guide wire, such that the guide wire can be used for a variety of different configurations of filters. Alternatively or additionally, the spring system may be incorporated into retractor wires that connect to the proximal end of the filter body. During retrieval of the filter, the spring system can be neutralized or disabled so that the operator can remove the filter from the patient's body.

The filter in one configuration includes a plurality of expandable filter walls connected to the filter body adjacent to the opening in the proximal end of the filter body. When the filter is in the deployed configuration, the expandable filter walls are compressed and do not obstruct fluid and particles from entering and exiting the opening in the proximal end of the filter body. Prior to removal of the filter from the vessel, the expandable filter walls are expanded, obstructing the proximal opening of the filter body. The expandable filter walls prevent the large particles that have become trapped inside the filter from exiting the filter body during retrieval of the filter.

FIG. 1 shows a peripheral vascular filter 100 in a deployed configuration. The peripheral vascular filter 100 comprises a self-expanding stent 102 in mechanical connection with a catheter 104. The self-expanding stent forms a lumen that extends from a proximal end 106 to a distal end 108 of the stent 102.

The catheter 104 forms a helix 110 that is in mechanical connection with the stent 102. In one configuration, the catheter 104 is connected to an inner surface of the stent 102, and winds around the inner surface to form the helix 110. In another configuration, the catheter 104 is connected to an outer surface of the stent 102, and winds around the outer surface of the stent 102 to form the helix 110. The helix 110 may be continuously connected to the stent 102 along the length of the helix 110, or may be attached to the stent 102 at a plurality of discrete points. The helix 110 may extend from the proximal end 106 of the stent 102 to the distal end 108 of the stent 102, or may terminate prior to reaching the distal end 108 of the stent 102. A guide wire 122 is disposed inside the catheter 104.

A cone-shaped net 112 is in mechanical connection with the stent 102. The cone-shaped net 112 has an open proximal end 114 that is attached to the stent 102, and a closed distal end 116. The cone-shaped net 112 tapers from the open proximal end 114 to the closed distal end 116. The cone-shaped net 112 effectively traps large particles that enter the stent lumen through the proximal end 106 of the stent 102, and prevents them from escaping.

The stent 102 comprises a permeable mesh material. The permeable mesh material allows small particles to flow through the walls of the stent 102, but prevents large particles from flowing through the walls of the stent 102.

The peripheral vascular filter 100 includes a plurality of retractor wires 118 connected to the catheter 104 at a location 120 proximal to the stent 102. Each retractor wire 118 connects to an expandable filter wall. The expandable filter walls are in a collapsed configuration in FIG. 1, and are therefore not shown. The expandable filter walls are shown in an expanded configuration in FIG. 8D.

Figure 2:
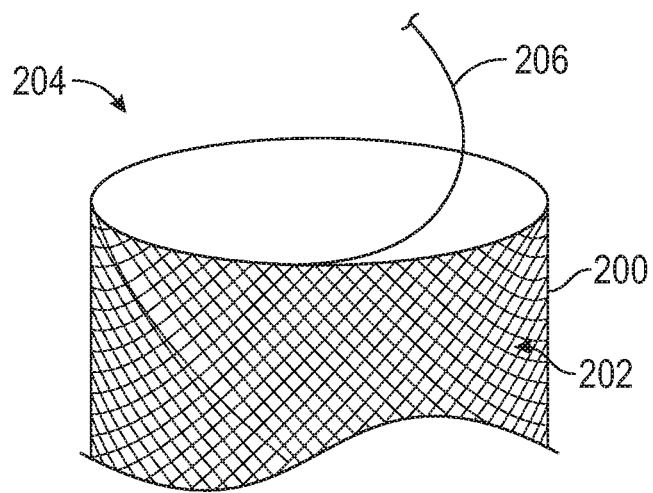
FIG. 2 shows the proximal end of the self-expanding stent.

FIG. 2 shows the proximal end of the self-expanding stent in more detail. The self-expanding stent 200 has a mesh surface 202 that acts as a filter. Large particles that enter the lumen of the stent 200 from the proximal end 204 of the stent 200 cannot pass through the mesh surface 202, and therefore become trapped inside the stent 200. Smaller particles may be able to pass through the filter, so that the filter does not completely obstruct the flow of fluid through the vascular lumen. The mesh surface 202 may have uniform openings along its surface. In one aspect, the size of the openings in the mesh surface decreases from the proximal end 204 towards the distal end of the stent 200. For example, the holes may have an average diameter of about 60-80 microns at the proximal end 204, and may decrease in size to an average diameter of about 10 microns at the distal end of the stent 200. A retractor wire 206 extends proximal to the proximal end 204 of the stent 200. Additional retractor wire (not shown) may also extend proximal to the proximal end 204 of the stent 200.

Figure 3:
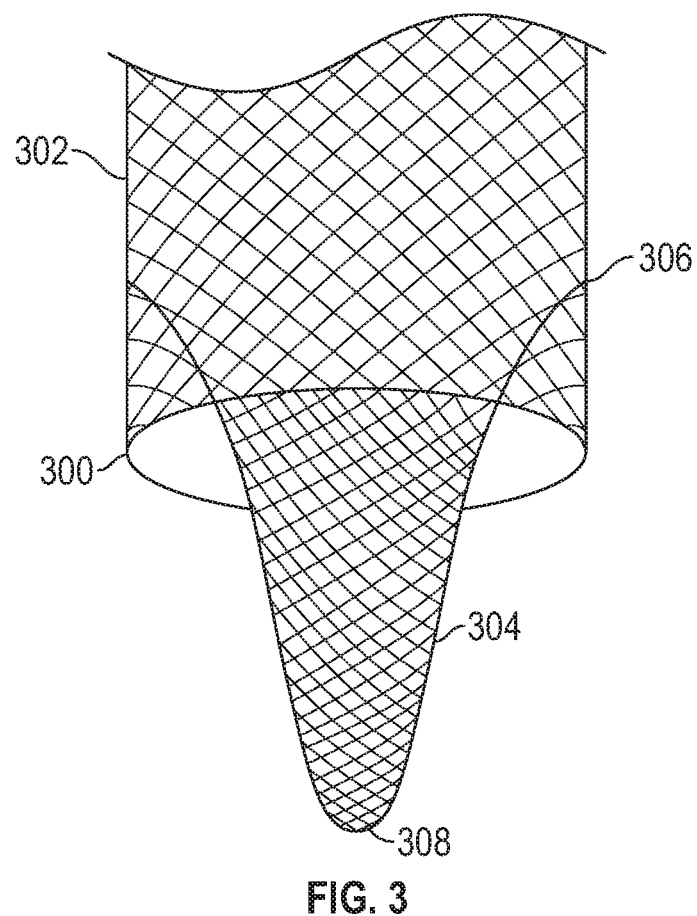
FIG. 3 shows the distal end of the self-expanding stent and the cone-shaped net.

FIG. 3 shows the distal end 300 of the self-expanding stent 302 and the cone-shaped net 304 in more detail. The cone-shaped net 304 may be mechanically connected to stent 302 at the proximal end 306 of the cone-shaped net 304. The mechanical connection may be proximal to the distal end 300 of the stent 302 as shown in FIG. 3, or may be at the distal end 300 of the stent 302. The openings in the cone-shaped net 304 in one configuration are smaller than the openings in the stent 302. The proximal end 306 of the cone-shaped net 304 may be mechanically connected to the inner surface of the stent 302, as shown in FIG. 3. The connection between the stent 302 and the cone-shaped net 304 may be sufficiently continuous so that no hole between the stent 302 and the net 304 is larger than a hole of the mesh-like surface of the stent 302. In one aspect, the connection between the stent 302 and the cone-shaped net 304 is sufficiently continuous so that no hole between the stent 302 and the net 304 is larger than a hole of the cone-shaped net 304.

As shown in FIG. 3, the cone-shaped net 304 may have an approximately conical configuration, but may not form an exact cone. As shown in FIG. 3, the distal tip 308 of the cone-shaped net may be rounded. The cone-shaped net 304 can have a general configuration with a radius that is larger at the mechanical connection between the stent 302 and the cone-shaped net 304 than at the distal tip 308 of the cone-shaped net 304.

Figure 4:
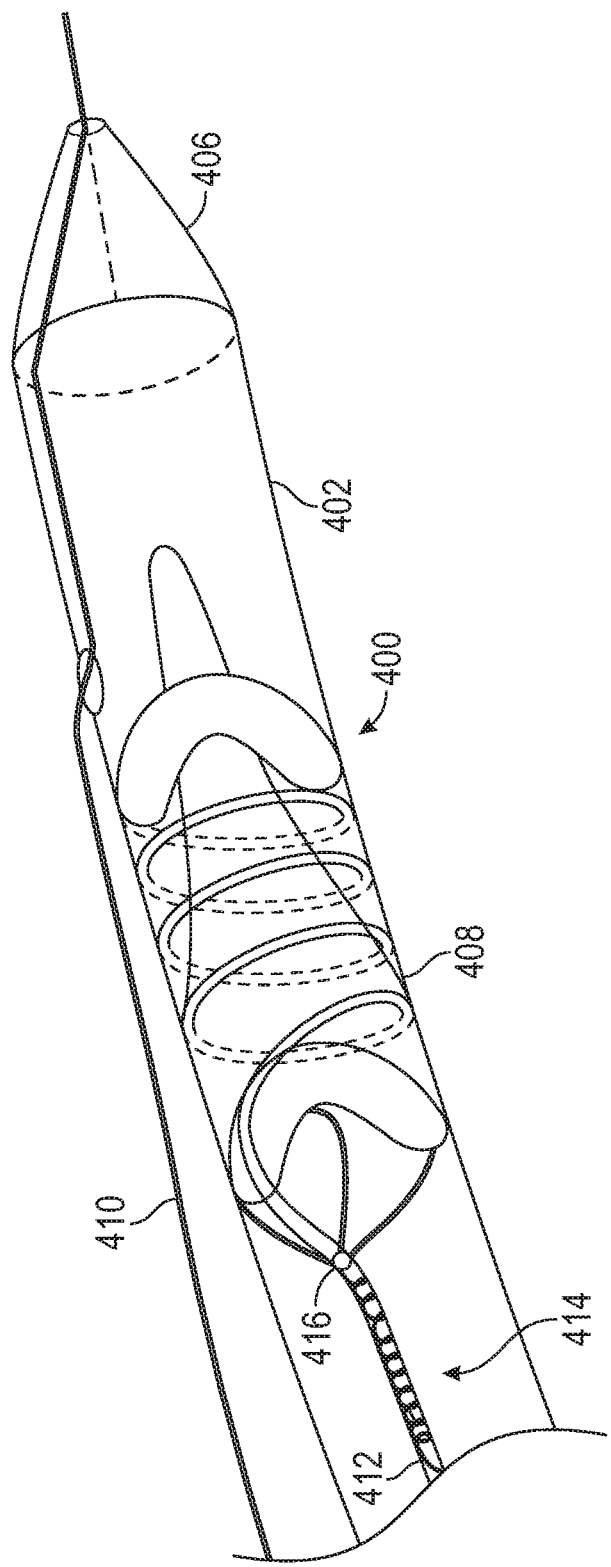
FIG. 4 shows the peripheral vascular filter disposed within a delivery catheter.

FIG. 4 shows the peripheral vascular filter 400 disposed within a delivery catheter 402. The peripheral vascular filter 400 can be delivered to a site for deployment using a rapid exchange delivery system, as shown in FIG. 4. The tapered end 406 of the delivery catheter 402 flares out when the filter 400 exits the delivery catheter 402.

As shown in FIG. 4, the self-expanding stent 408 can have a collapsed or folded configuration inside the delivery catheter 402, thereby reducing the size of the filter 400 for delivery. The filter 400 can be deployed via a pin and pull technique. The delivery catheter 402 with the filter 400 disposed therein can be guided through the vasculature using a guide wire 410. Once the delivery catheter 402 and filter 400 reach a desired position for deployment, the filter 400 can be held in place using the catheter 412, while the delivery catheter 402 is retracted, exposing the filter 400. In some configurations, the catheter 412 has an outer diameter of 0.14, 0.18, or 0.35.

The peripheral vascular filter 400 can have a spring wire system that absorbs random forces applied to the catheter 412. For example, if the operator inadvertently bumps the catheter, or if the patient moves the portion of their body in which the filter is disposed, a force may be applied to the catheter. FIG. 4 shows a spring wire system 414 in mechanical connection with the catheter 412 proximal to the connector ring 416. Once the filter is deployed, the system is designed such that the self-expanding stent 408 expands to exert a friction force on the vessel wall, and therefore the filter 400 remains stationary until it is deliberately removed by the physician. However, if the stent 408 is rigidly connected to the catheter 412, extraneous forces on the catheter 412 could cause the filter 400 to become dislodged from its intended position. Accordingly, a spring wire system 414 can be disposed between the catheter 412 and the stent 408 to absorb these extraneous forces. Although the spring wire system shown in some configurations to include a coil spring, the invention is not limited to a coil spring. Any device that is biocompatible and that can absorb forces applied to the catheter or guide wire without transmitting them to the filter body can be used. The device in one aspect may have a structure that deforms when forces are applied so that its length changes, allowing it to absorb forces without transmitting them to the filter body. The device may be a spring, or may have spring-like properties.

Figures 5A, 5B:
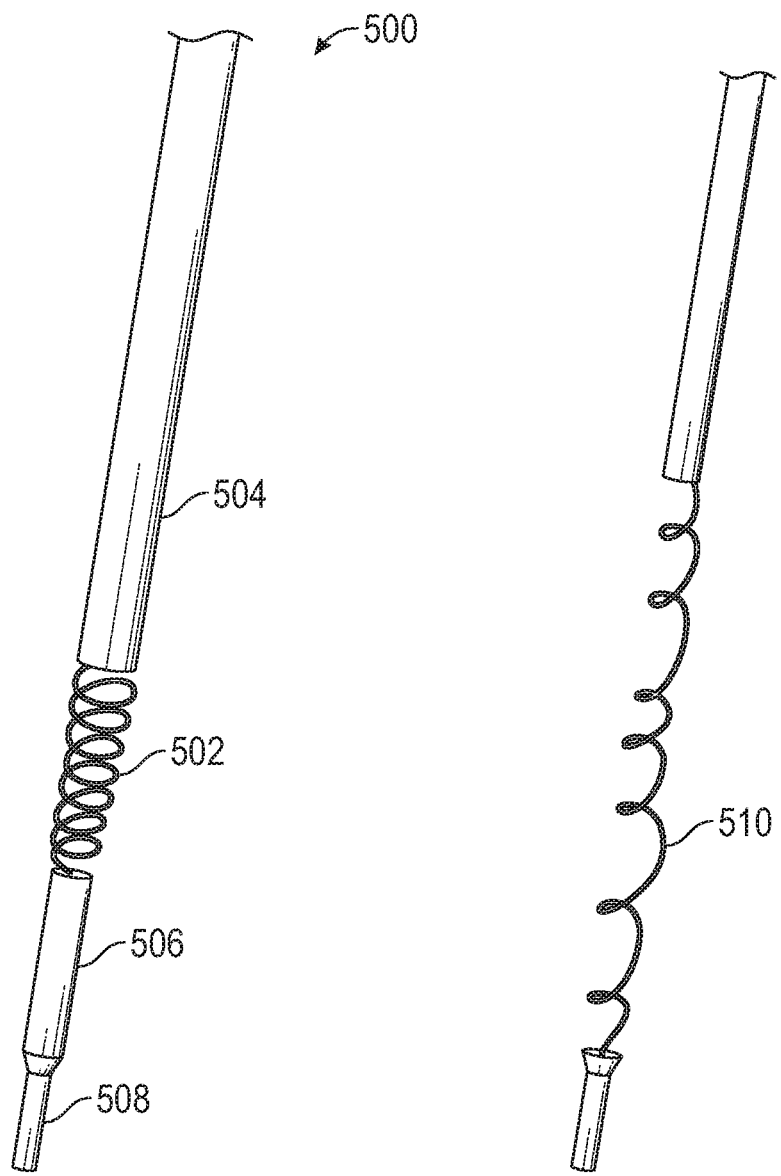
FIG. 5A shows a spring wire system in a first configuration.
FIG. 5B shows the spring wire system of FIG. 5A in a second configuration in which the spring is stretched.

FIGS. 5A and 5B show the spring wire system 500 in more detail. The spring wire system functions as a safety tension element to prevent forces from unintentionally being applied to the deployed filter. The spring wire system has a spring 502 that connects a first portion 504 of the catheter to a second portion 506 of the catheter. The spring wire system 500 includes a solid core wire 508 as a backup support system for retrieving the filter.

FIG. 5B shows the spring wire system 500 of FIG. 5A in a second configuration in which the spring 510 is stretched.

Figure 6A:
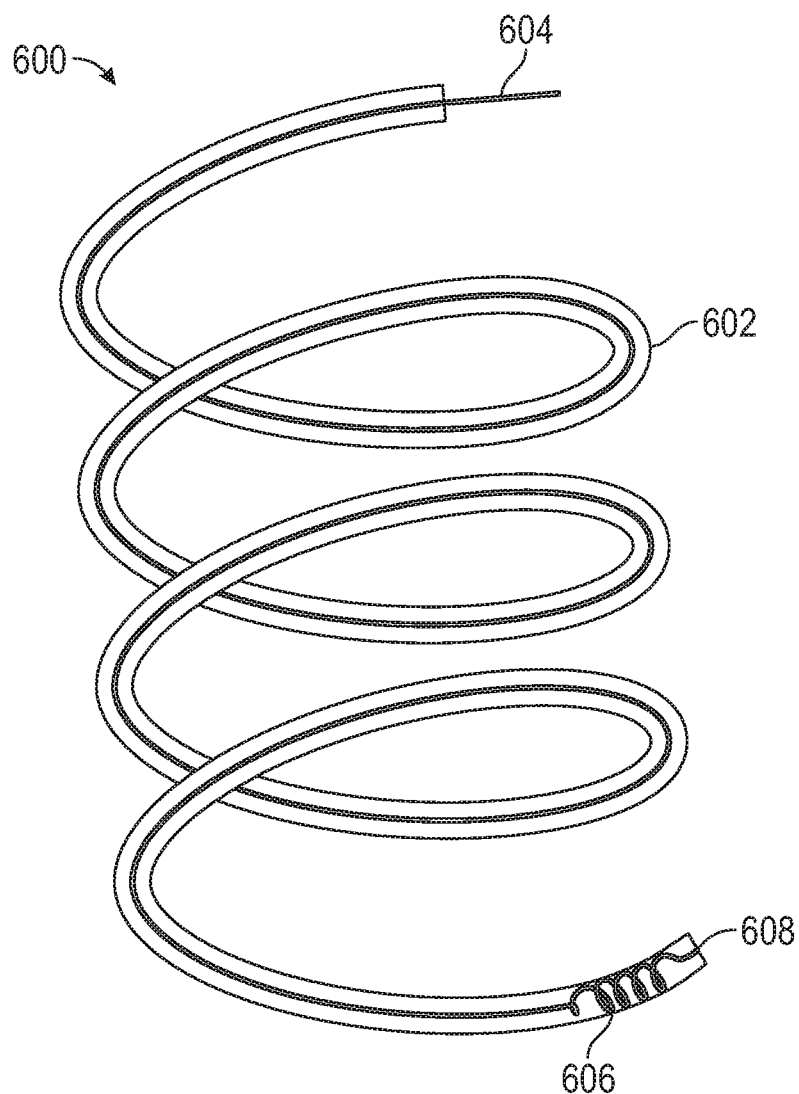
FIG. 6A shows a helical portion of a catheter.

FIG. 6A shows the helical portion 600 of the catheter 602. The helical portion 600 can be mechanically connected to a surface of the catheter, and can be concentric to the catheter, as shown in FIG. 1. According to one aspect, the helix 600 can accommodate up to 100 mm of 0.09 wire. The catheter 602 forming the helix can have an inner diameter of 0.14, though the invention is not limited to this size. The catheter 602 may have a larger or smaller inner diameter.

A guide wire 604 may be disposed inside the catheter 602. The guide wire 604 may have a spring portion 606 at its distal tip. The spring portion 606 may be integral to the wire 604, or may be welded to the wire 604. The spring portion 606 may connect the proximal end of the wire 604 to the distal tip 608 of the catheter 602. The guide wire 604 with the spring portion 606 has a similar function as the spring wire system 500 in FIG. 5, and may form part of that system. If the filter were rigidly connected to the guide wire 604, any force on the guide wire 604 would be directly translated to the filter. For example, a slight motion of the patient or the physician could inadvertently displace the filter. The wire 604 with the spring portion 606 attached to the distal tip 608 of the catheter 602 allows for forces to be exerted on the wire 604 without the position of the filter being affected. For example, if the wire 604 is moved distally, the spring portion 606 will compress, absorbing the force on the wire 604. If the wire 604 is moved proximally, the wire will expand, again preventing the force from resulting in motion of the filter.

Figure 6B:
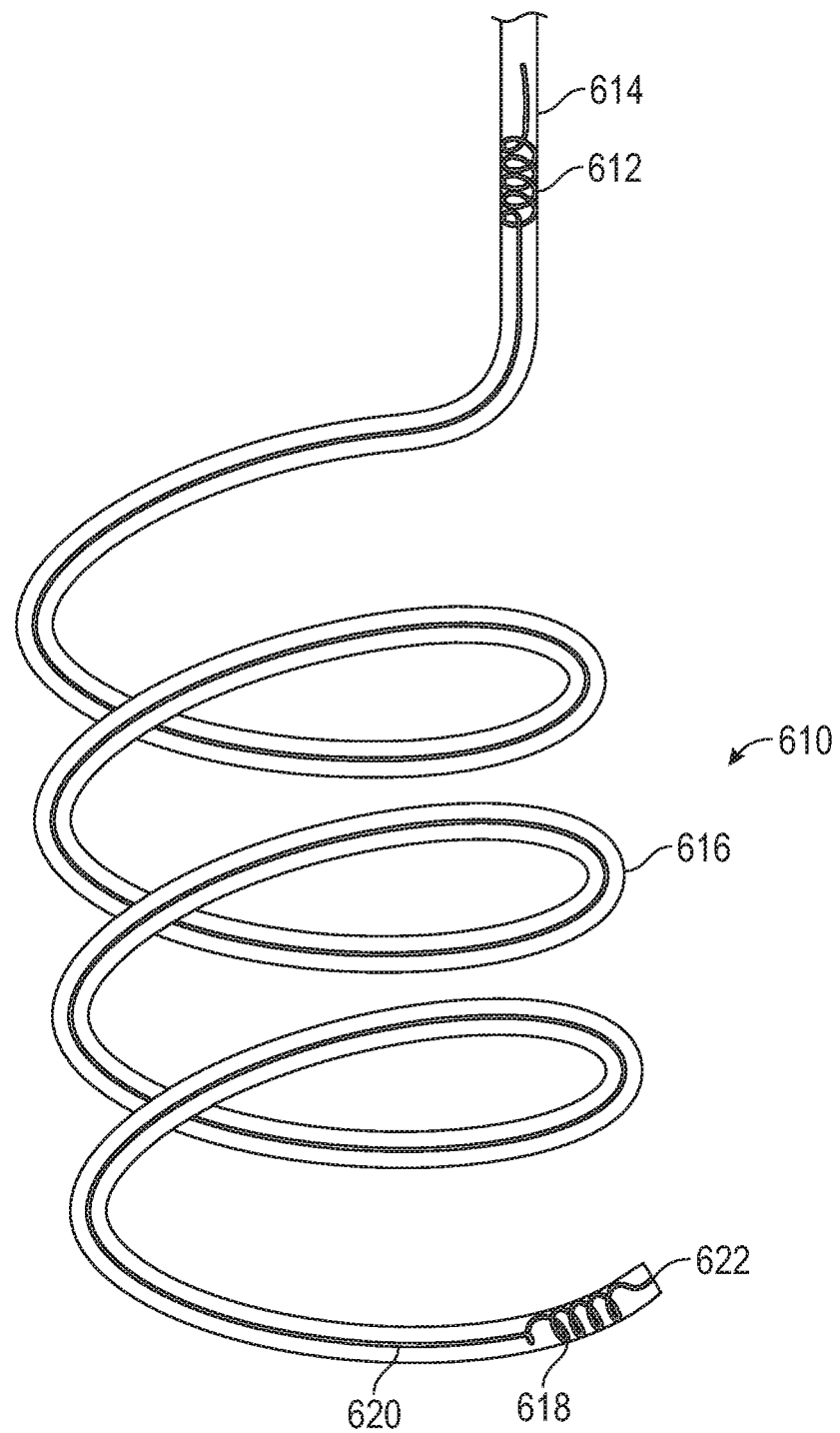
FIG. 6B shows a catheter with a double spring wire system.

FIG. 6B shows the catheter 610 with a double spring wire system. The spring wire system includes a first spring 612 disposed within the catheter 610 between a proximal portion 614 of the catheter 610 and the helical portion 616. The first spring 612 is connected to a guide wire 620. A second spring 618 connects the guide wire 620 to the distal end 622 of the catheter 610.

The filter of the present invention can be temporarily positioned in the peripheral vasculature of a patient, and then easily removed once it is no longer needed. During its time within the vasculature, the filter may have collected particles of various sizes, most of which are larger than the holes in walls of the self-expanding stent. An important feature of the filter is successful removal without introducing the collected particles back into the bloodstream. Accordingly, the filter in one aspect has a plurality of expandable filter walls, each connected to a retractor wire.

Figure 7:
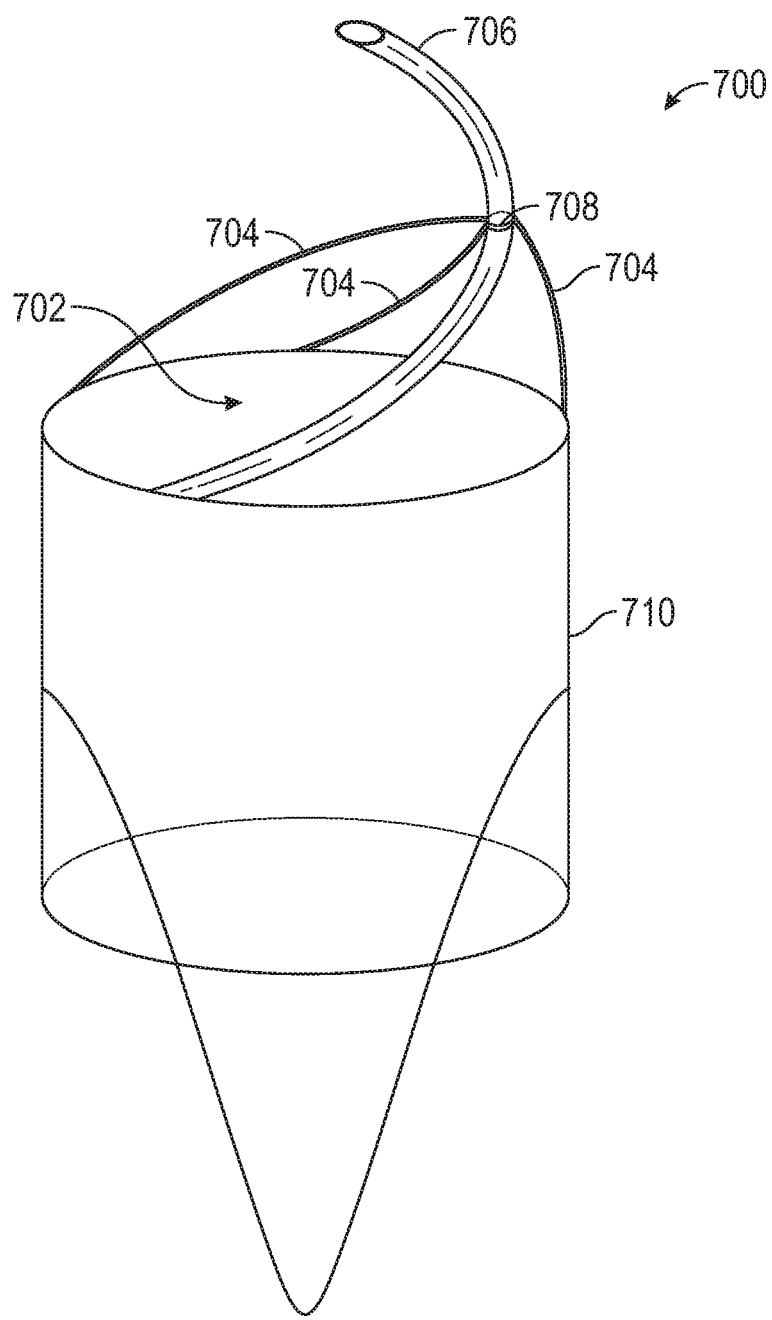
FIG. 7 shows a deployed peripheral vascular filter prior to retrieval.

FIG. 7 shows a filter 700 prior to retrieval. Fluid enters the filter through the proximal opening 702. In the configuration of FIG. 7, the filter has four quadrants. Three of the quadrants have a retractor wire 704, while the catheter 706 acts as a fourth and primary retractor wire. The three retractor wires 704 attach to the catheter 706 at a position 708 proximal to the stent 710 at one end and to an expandable filter wall at the other end. The catheter 706 is also attached to an expandable filter wall. The expandable filter walls are not shown in FIG. 7, because they are inactive while the filter is deployed and open.

Figure 8A:
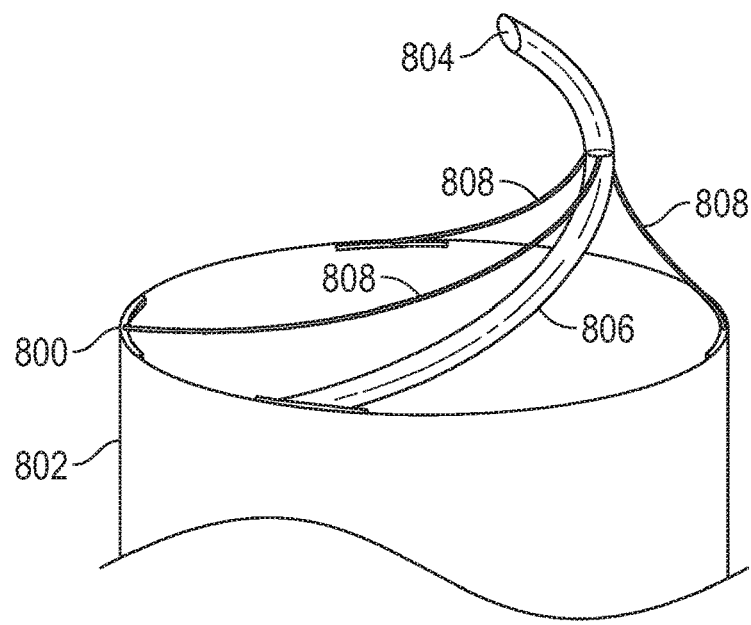
FIG. 8A shows a proximal end of a stent in a deployed configuration.

FIGS. 8A-8D show the process of deploying the filter walls using the retractor wires. FIG. 8A shows the proximal end 800 of the stent 802 in a deployed configuration. Particles enter the filter through the opening in the proximal end 800 of the stent 802. The expandable filter walls are compressed, and do not obstruct particles from entering or exiting the proximal end 800 of the stent 802.

Figure 8B:
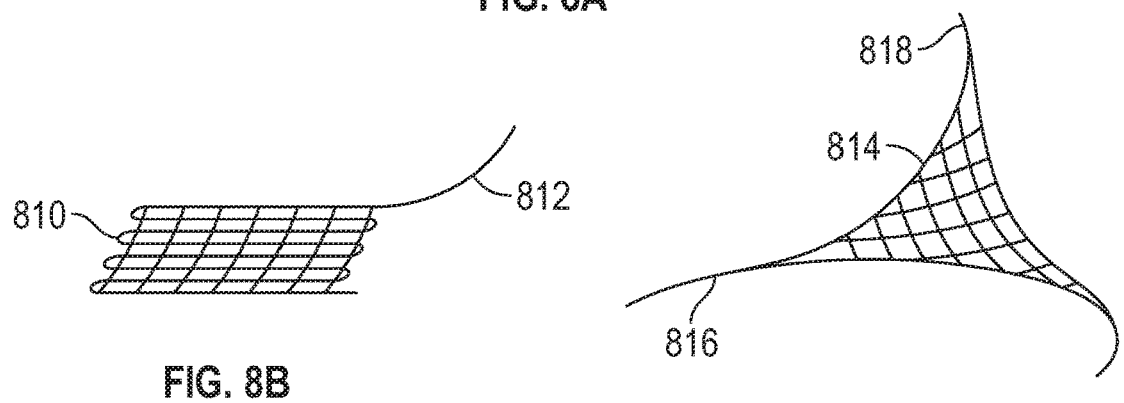
FIG. 8B shows an expandable filter wall in a compact configuration.
Figure 8C:
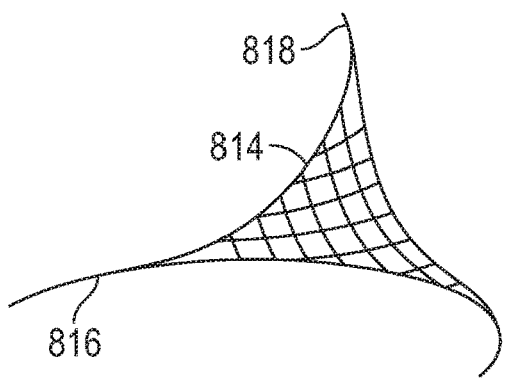
FIG. 8C shows a deployed expandable filter wall.

In order to remove the filter, a retrieval shaft is moved distally toward the filter until it engages the proximal end 804 of the catheter 806. Once the proximal end 804 of the catheter 806 has been engaged, the retrieval shaft is pulled proximally. The catheter 806 is pulled proximally by the retrieval shaft. This motion exerts tension on the catheter 806 and retractor wires 808. The retractor wires 808 and catheter 806 in turn deploy the expandable filter walls. FIG. 8B illustrates an expandable filter wall 810 in a compact configuration. The expandable filter wall 810 is connected to a retractor wire 812. FIG. 8C illustrates the expandable filter wall 814 in an expanded configuration. The expandable filter wall 814 is connected to a proximal surface 816 of the stent at one end, and to a retractor wire 818 at the opposite end.

Figure 8D:
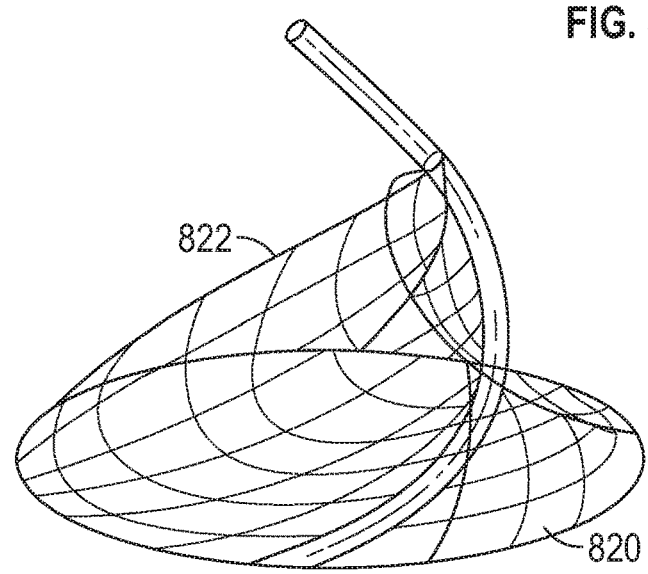
FIG. 8D shows all four expandable filter walls in an expanded configuration.

FIG. 8D shows all four expandable filter walls in the expanded configuration. In this configuration, the proximal opening 820 of the stent is completely obstructed by the expandable filter walls 822, so that particles trapped in the filter cannot escape during retrieval of the filter. The expandable filter walls 822 occlude the filter inflow to trap all materials inside the filter. In the configuration of FIGS. 8A and 8D, the filter has four quadrants that are covered by four expandable filter walls when the expandable filter walls are deployed. However, the invention may include more or fewer filter walls as long as the proximal opening of the filter is completely covered by the filter walls when they have been deployed. In one aspect, the filter walls comprise a mesh material that has openings that are less than 20 µm.

Figure 9:
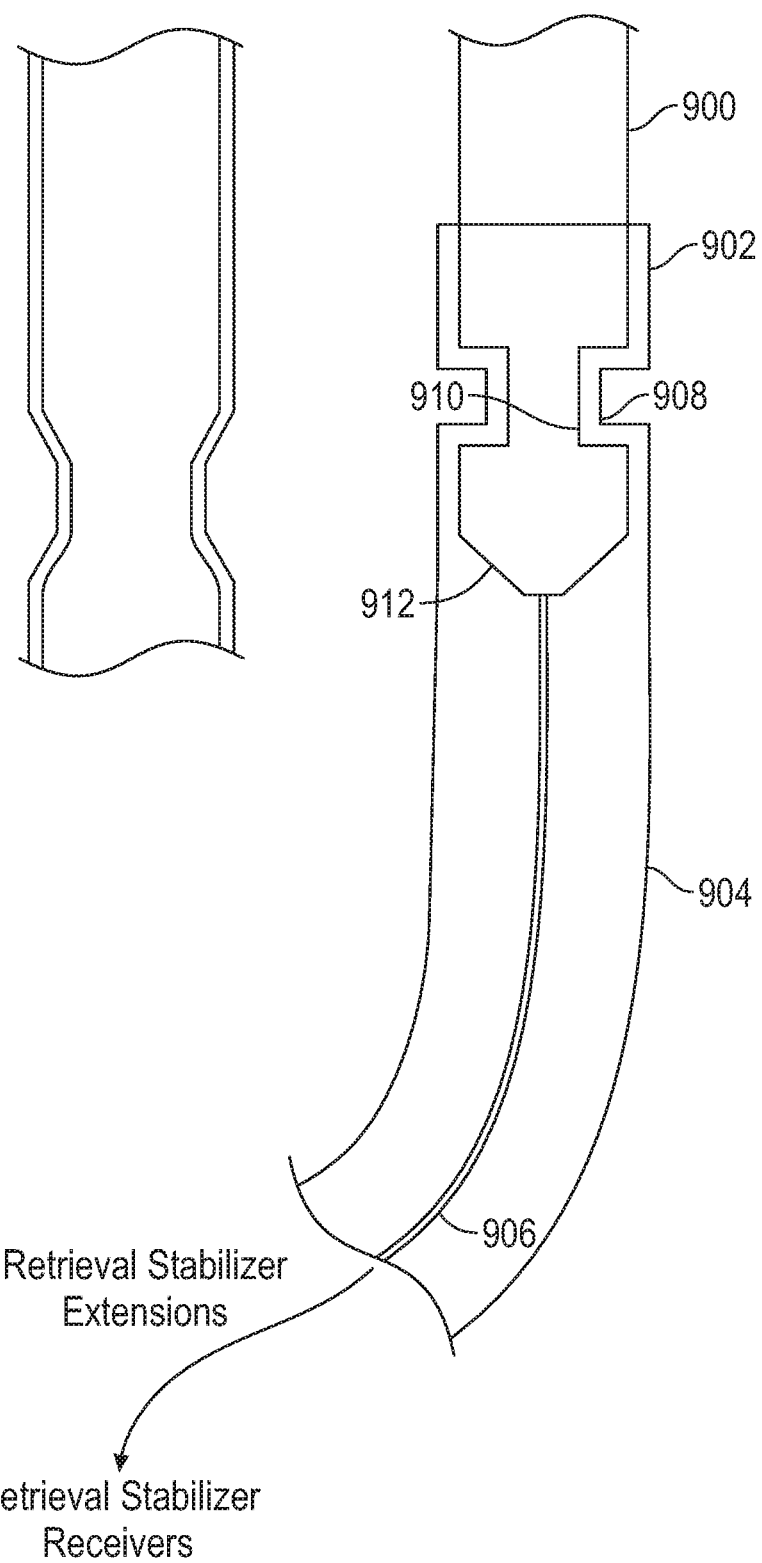
FIG. 9 shows the mechanism for engaging a retrieval shaft with a support ring.

FIG. 9 shows a mechanism for engaging a retrieval shaft 900 with the proximal end 902 of the catheter 904. The retrieval shaft 900 if guided down the guide wire 906 until it reaches the proximal end 902 of the catheter 904. The retrieval shaft 900 and catheter 904 are configured to engage one other with a locking mechanism. A locking mechanism according to one aspect is shown in FIG. 9, but the invention is not limited to this configuration. The locking mechanism can be any mechanism for engaging the catheter with the retrieval shaft such that a retraction force on the retrieval shaft results in a retraction force on the catheter. In the example in FIG. 9, the proximal end 902 of the catheter 904 has indentations 908 that correspond to indentations 910 in the retrieval shaft. The distal end 912 of the retrieval shaft 900 enters the proximal end 902 of the catheter 904. The locking mechanisms 908, 910 engage, and the retrieval shaft 900 is secured to the catheter 904. Once the retrieval shaft 900 has engaged the catheter 904, the retrieval shaft 900 can be moved proximally. This action deploys the expandable filter walls.

Figure 10A:
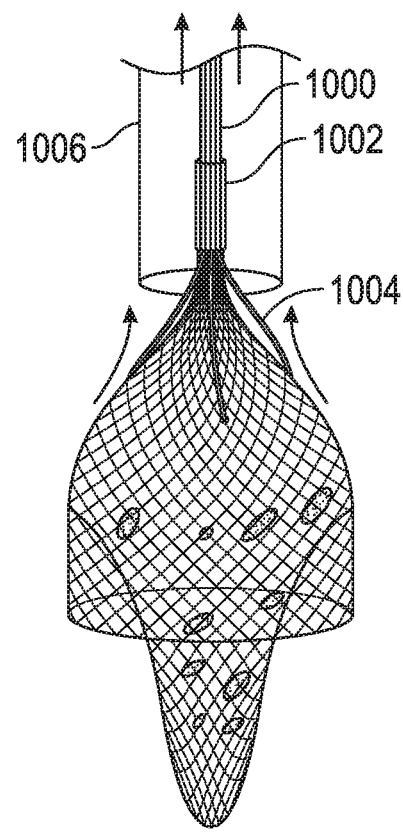
FIG. 10A shows retrieval of the peripheral vascular filter wherein the retrieval shaft has engaged the support ring, and the expandable filter walls have been deployed.
Figure 10B:
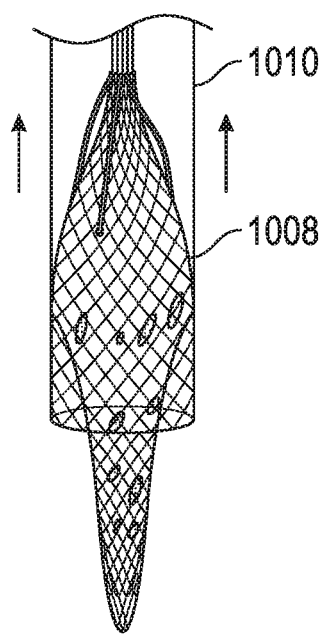
FIG. 10B shows a proximal portion of the filter having entered the retrieval catheter.
Figure 10C:
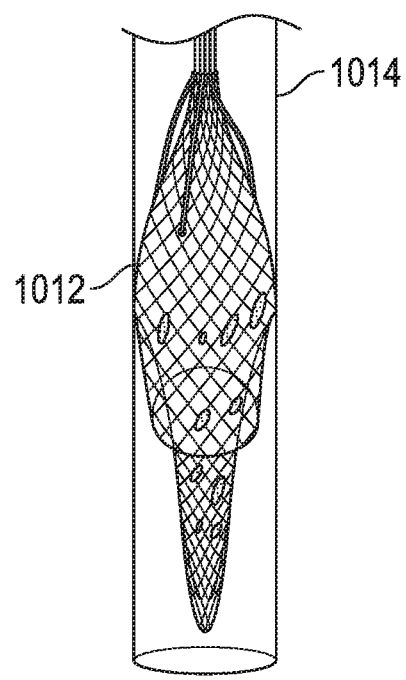
FIG. 10C shows the entire filter having entered the retrieval catheter.

FIGS. 10A-10C illustrate retrieval of the peripheral vascular filter. In FIG. 10A, the retrieval shaft 1000 has engaged the support ring 1002, and the expandable filter walls 1004 have been deployed. The retrieval shaft 1000 is withdrawn into a retrieval catheter 1006. In FIG. 10B, the proximal portion 1008 of the filter has entered the retrieval catheter 1010. In FIG. 10C, the entire filter 1012 has entered the retrieval catheter 1014. Particles trapped by the filter prior to retrieval remain inside the filter, due to the expandable filter walls covering the proximal opening of the filter. The filter obtains an oval configuration during retrieval with complete coverage of any material inside the filter.

Figure 11:
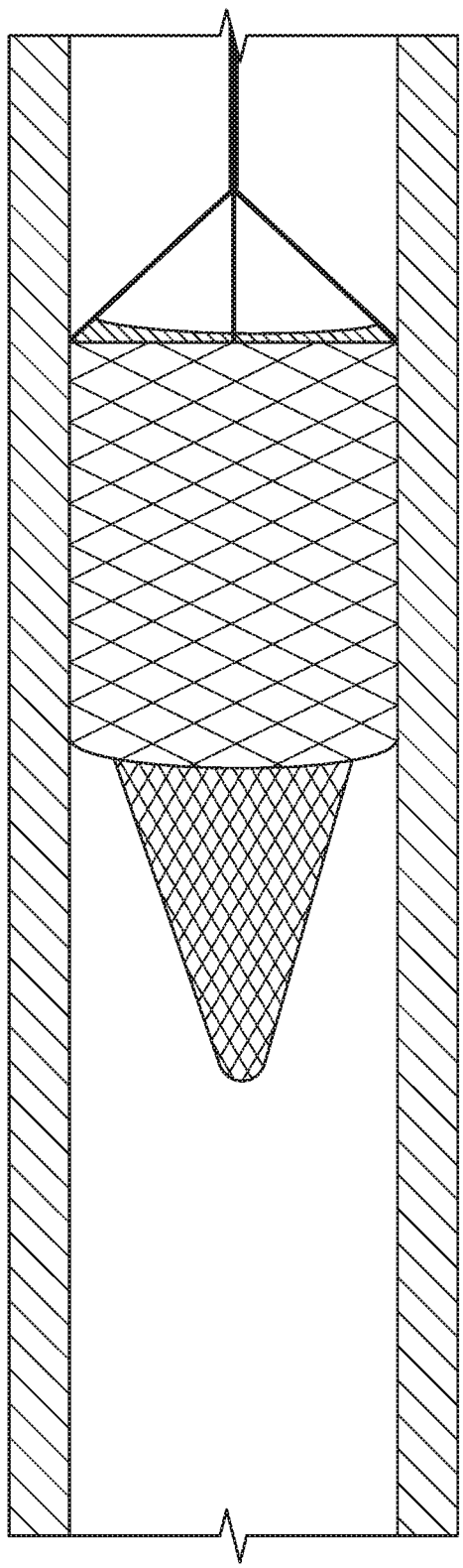
FIG. 11 shows a peripheral vascular filter that has just been deployed.
Figure 12:
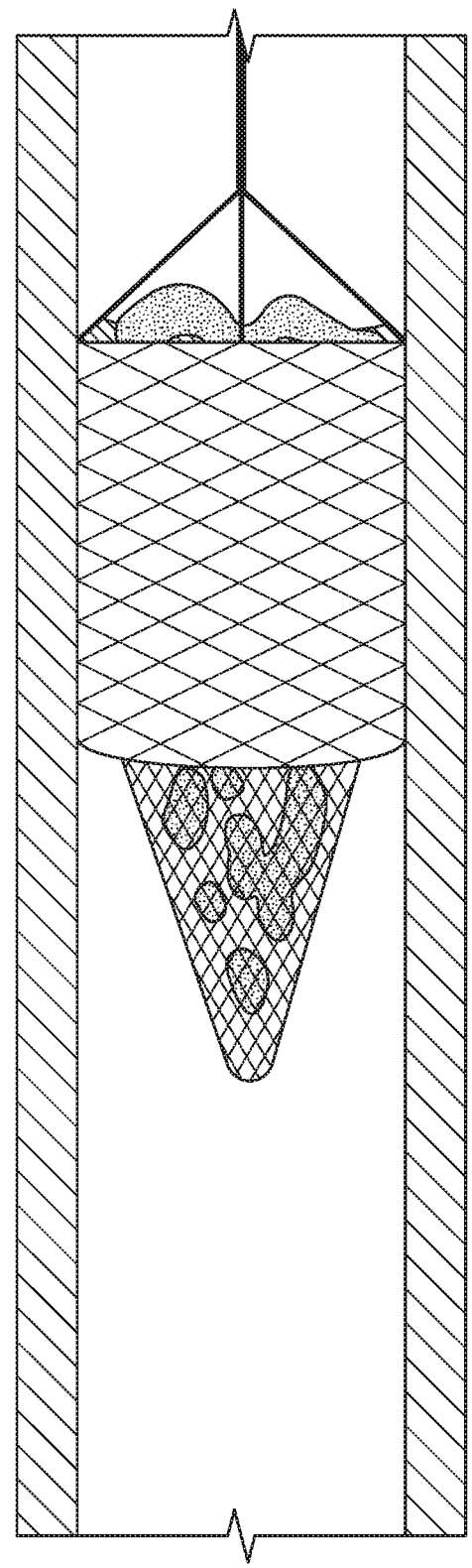
FIG. 12 shows a peripheral vascular filter in a deployed configuration once it has trapped particles.

FIGS. 11 and 12 show a peripheral vascular filter deployed in a vascular lumen.

The filter in FIG. 11 has just been deployed. The proximal end of the filter is open and unobstructed, but particles have not yet been trapped by the filter. FIG. 12 shows the deployed filter once it has trapped particles. The particles enter the filter through the proximal opening of the stent, and become trapped within the stent and the cone-shaped filter. The outer surface of the stent contacts and exerts radial force on the walls of the vessel in which the filter has been deployed. This creates a frictional force that keeps the filter in place after deployment.

Figure 13:
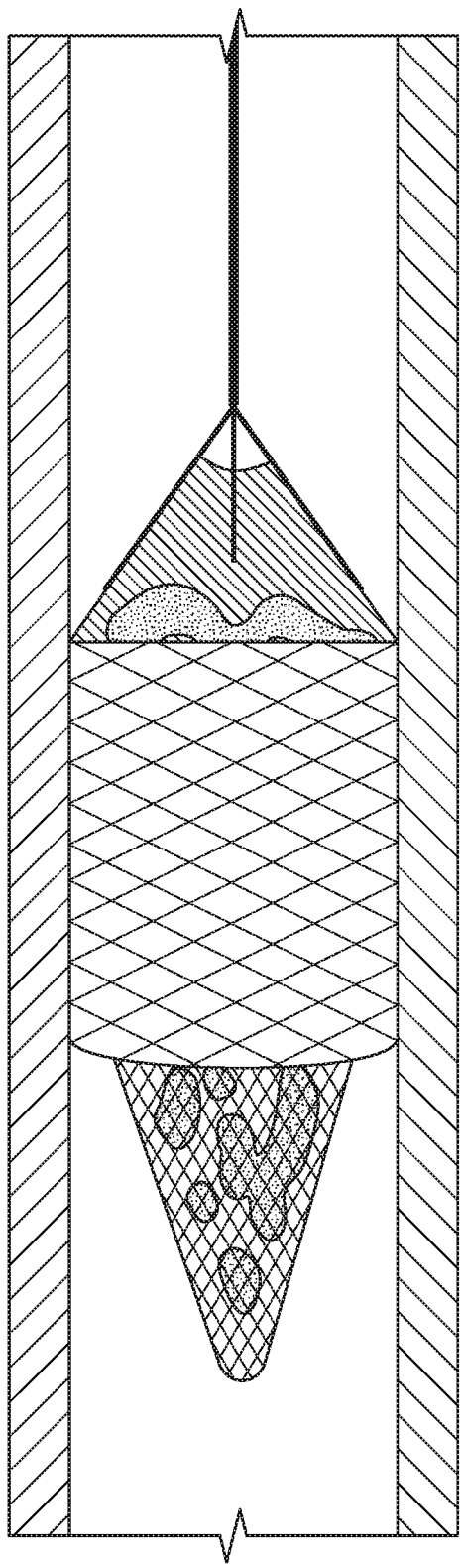
FIG. 13 shows a peripheral vascular filter in preparation for retrieval in a first configuration.
Figure 14:
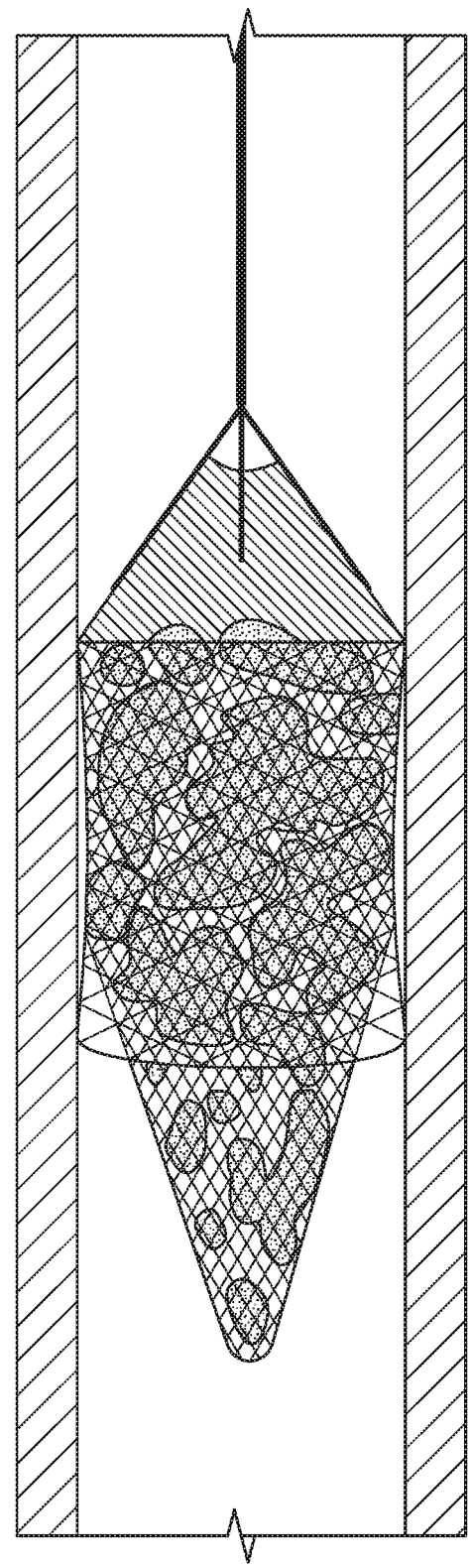
FIG. 14 shows a peripheral vascular filter in preparation for retrieval in a second configuration.

FIGS. 13 and 14 show the filter in preparation for retrieval. The expandable tent walls have been deployed, trapping particles inside the filter. The stent in FIG. 13 has parallel walls, while the stent in FIG. 14 has curved walls. The stent in FIG. 14 has a configuration in which the diameter of the filter is greater at the proximal and distal ends of the stent than the diameter of the filter between the proximal and distal ends.

In one aspect, the stent has a diameter between about 2.0 mm and about 26.0 mm. In one aspect, the stent has a diameter between about 2 mm and about 4 mm; between about 4 mm and about 7 mm; between about 7 mm and about 12 mm; between about 12 mm and about 18 mm; between about 18 mm and about 22 mm; or between about 22 mm and about 26 mm. The diameter of the stent may be equal to the diameter of the filter. In one aspect the filter has a length between about 20 mm and about 40 mm. In one aspect the filter has a length between about 20 mm and about 30 mm. In one aspect the filter has a length of about 40 mm; in another aspect the filter has a length of about 20 mm.

Figure 15:
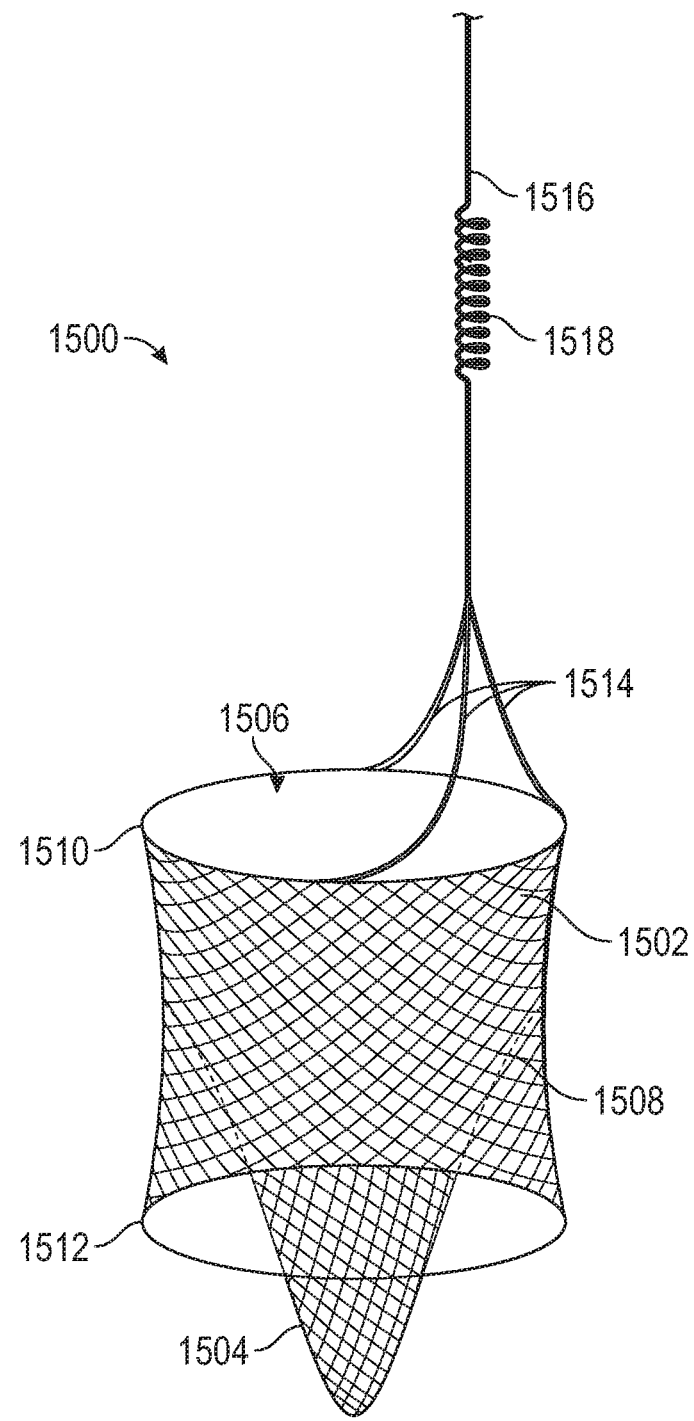
FIG. 15 shows another configuration of a peripheral vascular filter in a deployed state.

FIG. 15 shows another configuration of a peripheral vascular filter 1500 in a deployed state. The peripheral vascular filter 1500 includes a primary filter 1502, and a secondary filter 1504. The primary filter 1502 and secondary filter 1504 form the filter body. The primary filter 1502 forms a lumen therein. While the filter is deployed, the proximal end of the lumen is open to allow an inflow 1506 of fluid into the lumen.

The wall of the primary filter 1502 can include a plurality of struts, with holes formed therebetween. The struts may form a mesh. The holes 1508 between the struts may be smaller than 5 µm. The filter wall may oppose the vessel wall. The filter wall may abutt the vessel wall, creating a friction force that maintains the position of the filter.

The outflow from the filter is via the tapered secondary filter 1504. The secondary filter allows for more storage and also traps particles deep within the filter to prevent particles from escaping while the filter is deployed, or during removal. The primary filter 1502 may include stabilizing rings 1510, 1512 at opposite ends thereof. The stabilizing rings may aid in maintaining the position of the filter in the vessel, for example, by creating a friction force against the wall of the vessel.

The filter may include a plurality of retractor wires 1514 that connect the proximal end of the primary filter 1502 to a spring system 1518 and filter spring wire 1516.

Figure 16:
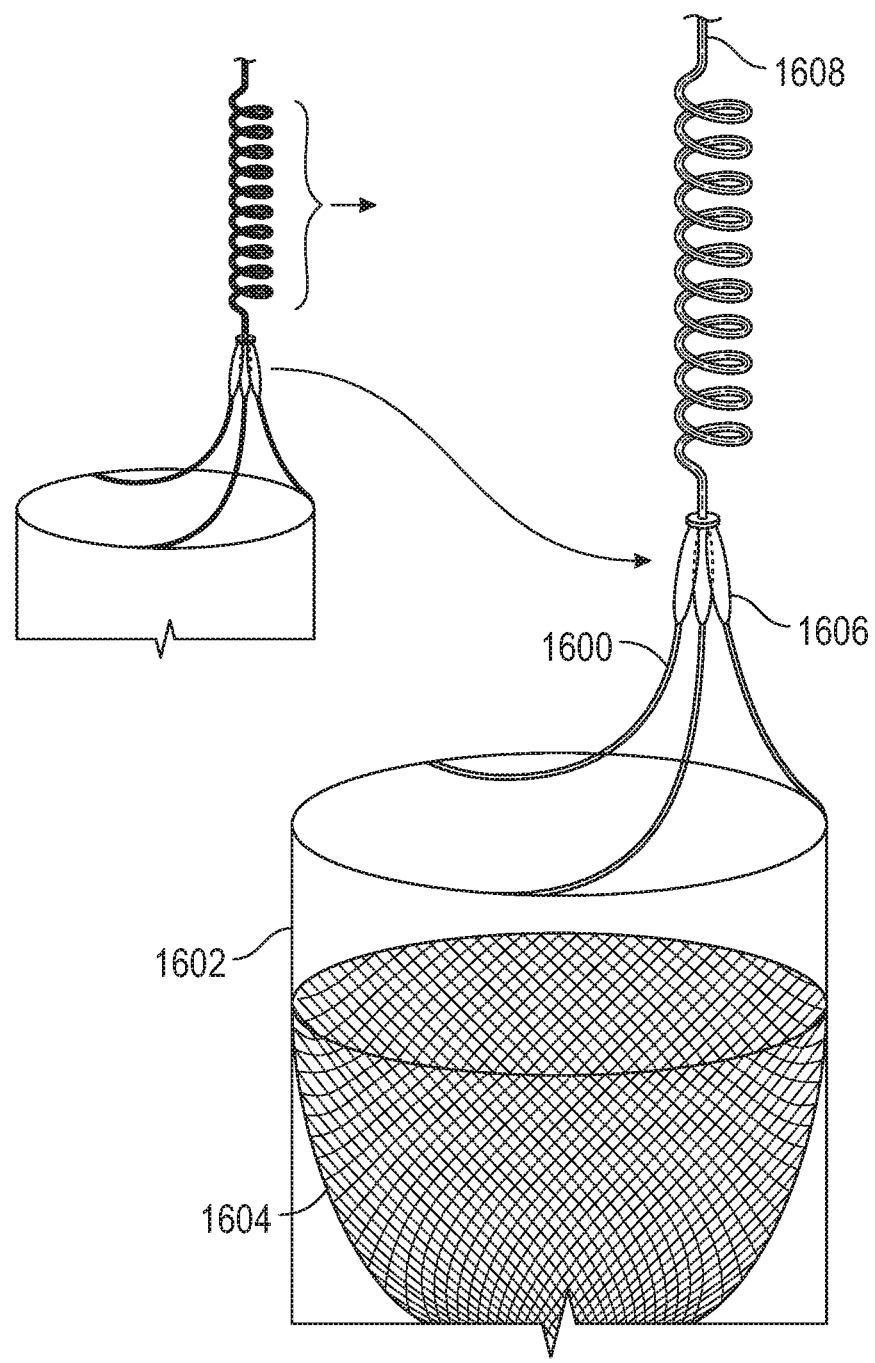
FIG. 16 shows details of a spring system according to some aspects.

FIG. 16 shows details of a spring system according to some aspects. The spring system includes a number of retractor wires 1600 connected to the proximal end of the primary filter 1602. The secondary filter 1604 is disposed inside the primary filter 1602, and the proximal end of the secondary filter 1604 is connected to the inner surface of the primary filter 1602. Each retractor wire 1600 may have a loop 1606 at its proximal end. The loop 1606 may be made of a flexible wire that allows the opposing sides of the loop spread apart from or draw near to each other when tension is applied to the retractor wire 1600. When a distally-directed force is applied to the guide wire 1608, the sides of the loop 1606 can spread apart, absorbing the force so that it is not transmitted to the filter body. When a proximally-directed force is applied to the guide wire 1608, the sides of the loop 1606 can draw near to each other, absorbing the force so that it is not transmitted to the filter body.

Figure 17C:
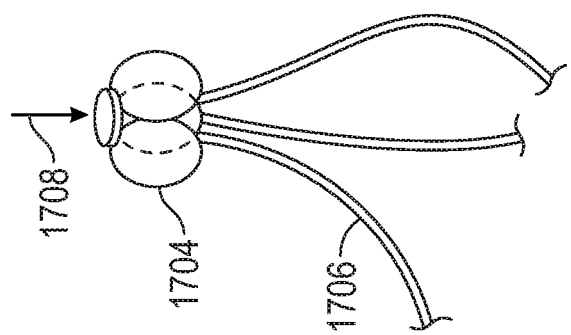
FIG. 17C shows the spring system absorbing a downward force.
Figure 17B:
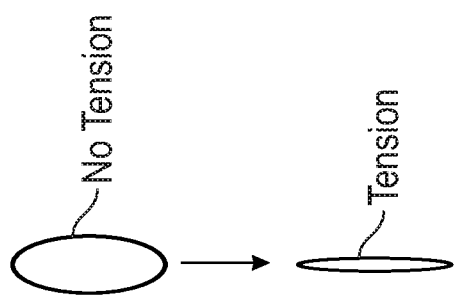
FIG. 17B shows tension being applied to the spring system.
Figure 17A:
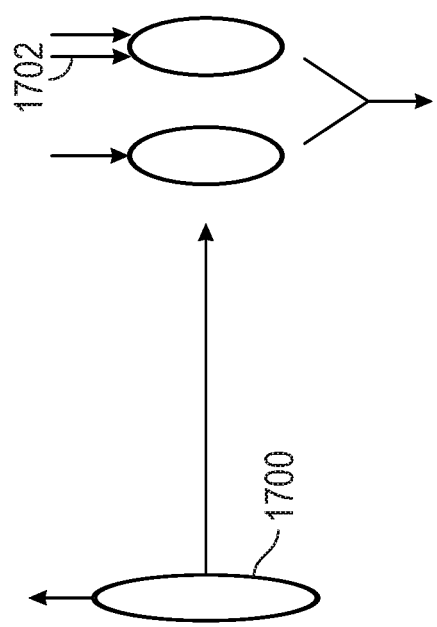
FIG. 17A shows additional aspects of the spring system.

FIGS. 17A-17C show additional aspects of the spring system. As shown in FIG. 17A, the loops can absorb upward forces 1700 and downward forces 1702. As shown in FIG. 17B, when tension is applied, the width of the loop contracts, and the length increases. The width of the loop can continue to decrease until the loop has the shape of a single wire. The loop can thus absorb upward and downward forces without changing the position of the filter.

As shown in FIG. 17C, the loop 1704 can be formed from a single wire or from two wires, and can be welded to the end of the retractor wire 1706. Alternatively, the loop 1704 may be integrally formed with the retractor wire 1706. When a downward force 1708 is applied to the spring system, the loop 1704 expands. When all three loops swell, they act as a brake for the guide wire. This can alert the operator to the fact that a force is being applied to the guide wire that could potentially dislodge the filter. The operator can pull the guide wire away from the filter to restore the loop 1704 to its natural shape, i.e., its shape when no forces are exerted on it.

Figure 18A:
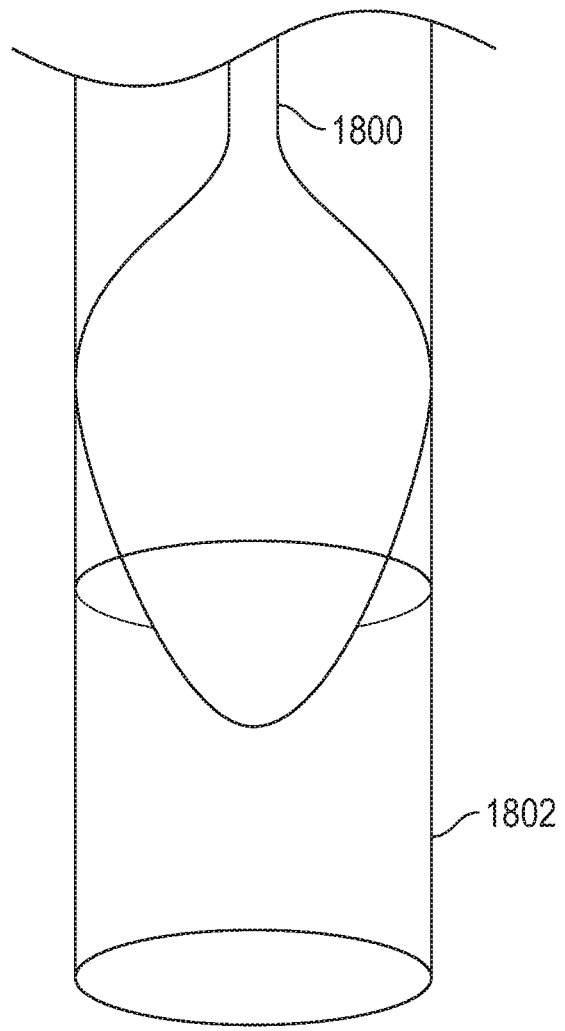
FIG. 18A shows aspects of deployment of the filter.
Figure 18B:
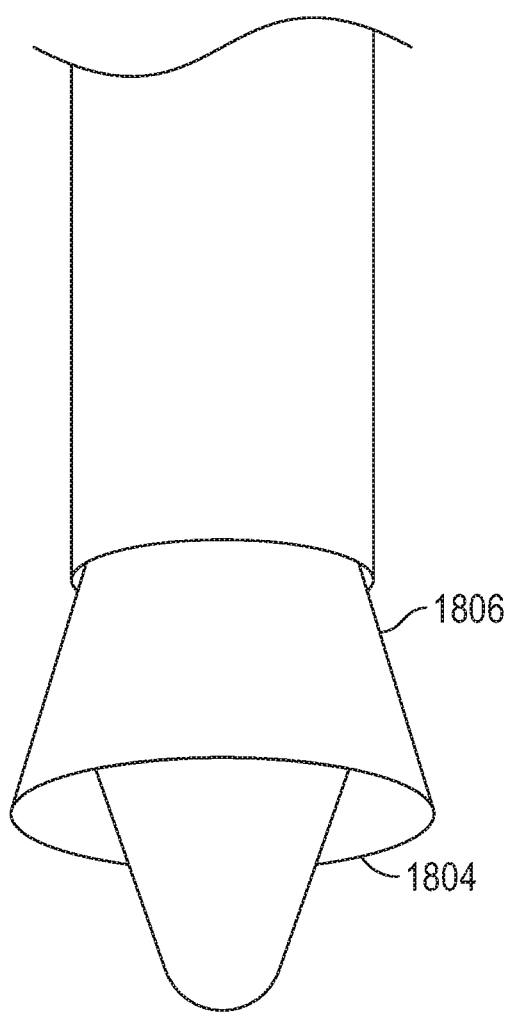
FIG. 18B shows additional aspects of deployment of the filter.

FIGS. 18A-18D show aspects of deployment of the filter. To deploy the filter, the operator pins the filter wire 1802 and pulls the filter delivery catheter 1801 proximally, as shown in FIG. 18A. The operator continues pulling the filter delivery catheter until the distal end 1804 of the filter 1806 is deployed, as shown in FIG. 18B. At this point the operator can still retrieve the filter if the location of the filter 1806 is not the target location.

Figure 18C:
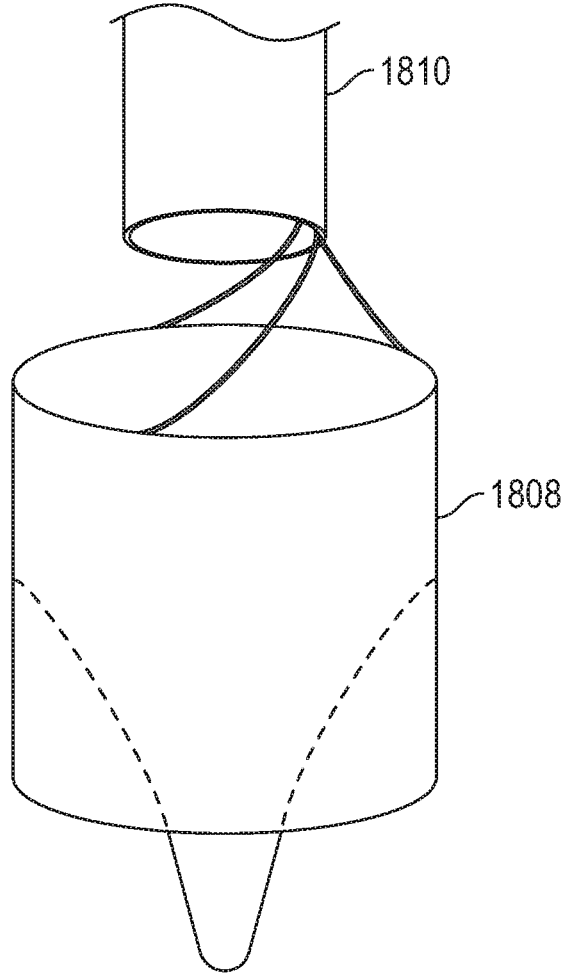
FIG. 18C shows additional aspects of deployment of the filter.
Figure 18D:
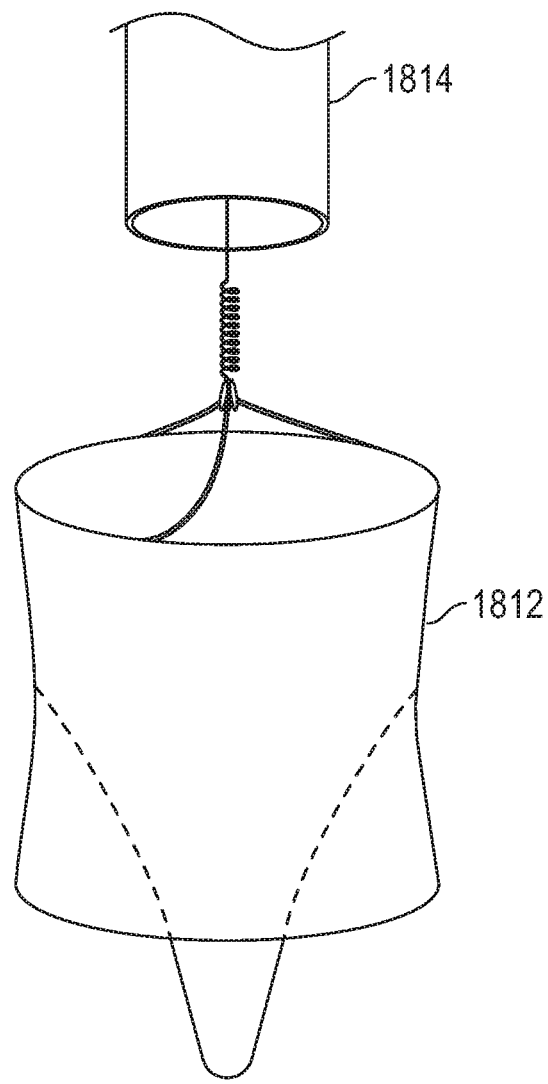
FIG. 18D shows additional aspects of deployment of the filter.

FIG. 18C shows the filter 1808 almost completely deployed. At this point it may not be possible to retrieve the filter 1808 with the delivery catheter 1810, and a retrieval catheter may be required to remove the filter. FIG. 18D shows the filter 1812 in a deployed state. At this point the delivery catheter 1814 is retracted.

Figure 19A:
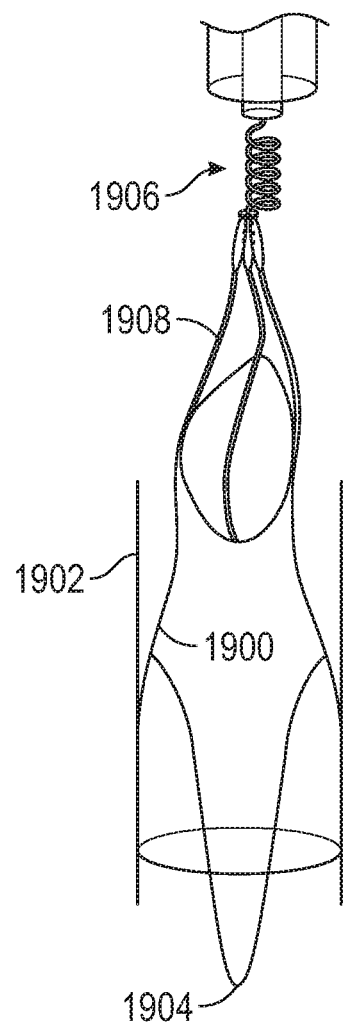
FIG. 19A shows aspects of retrieval of the filter.
Figure 19B:
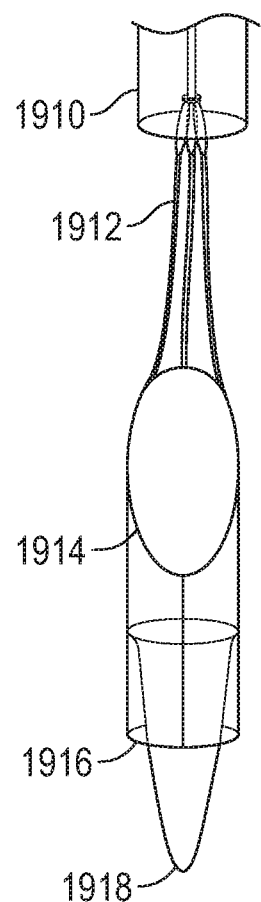
FIG. 19B shows additional aspects of retrieval of the filter.
Figure 19C:
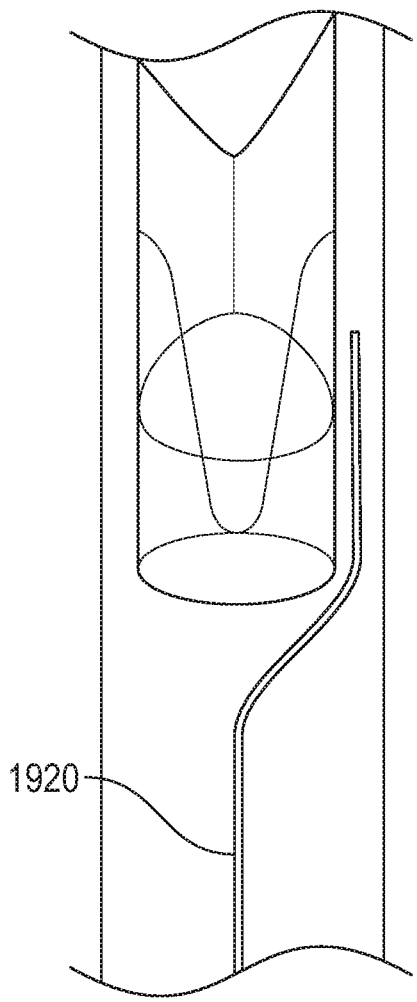
FIG. 19C shows additional aspects of retrieval of the filter.
Figure 20:
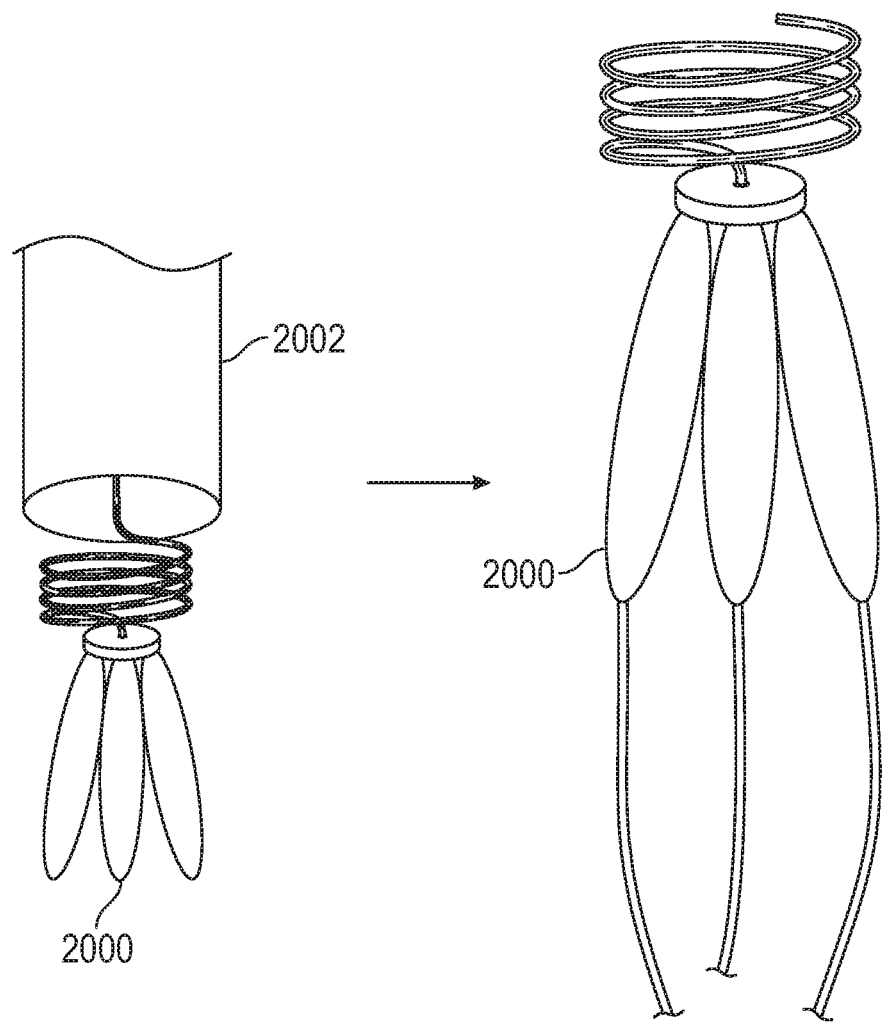
FIG. 20 shows the spring system entering the retrieval catheter during retrieval.

FIG. 19A-19C show aspects of retrieval of the filter. FIG. 19A shows the primary filter 1900 collapsing. The primary filter 1900 is pulled away from the vessel wall 1902 as it collapses and enters the retrieval catheter. The secondary filter 1904 is attached to the primary filter 1900, and is pulled proximally as the primary filter 1900 is pulled proximally. The loops 1906 at the proximal ends of the retractor wires 1908 act as a single, reinforced wire ready to pull the filter into the retrieval catheter. FIG. 20 shows the loops 2000 coming together as they enter the retrieval catheter 2002, which makes them stronger.

FIG. 19B shows the filter as the loops are being pulled into the retrieval catheter 1910. The retractor wires 1912 are now straight and close to each other, and their alignment with the catheter and with each other creates a significant strong stable pulling force that collapses the filter opening 1914. This is the first step in pulling the self-expanding portion of the filter into the retrieval catheter. The collapse of the opening of the filter closes the mouth of the primary filter and traps everything inside of it. The distal end 1916 of the primary filter also collapses, further ensuring secure trapping of the material inside the filter. The secondary filter 1918 with material trapped therein may extend distal to the distal end 1916 of the primary filter. Finally, as shown in FIG. 19C, the filter is removed with the guide wire 1920 in place.

Figure 21A:
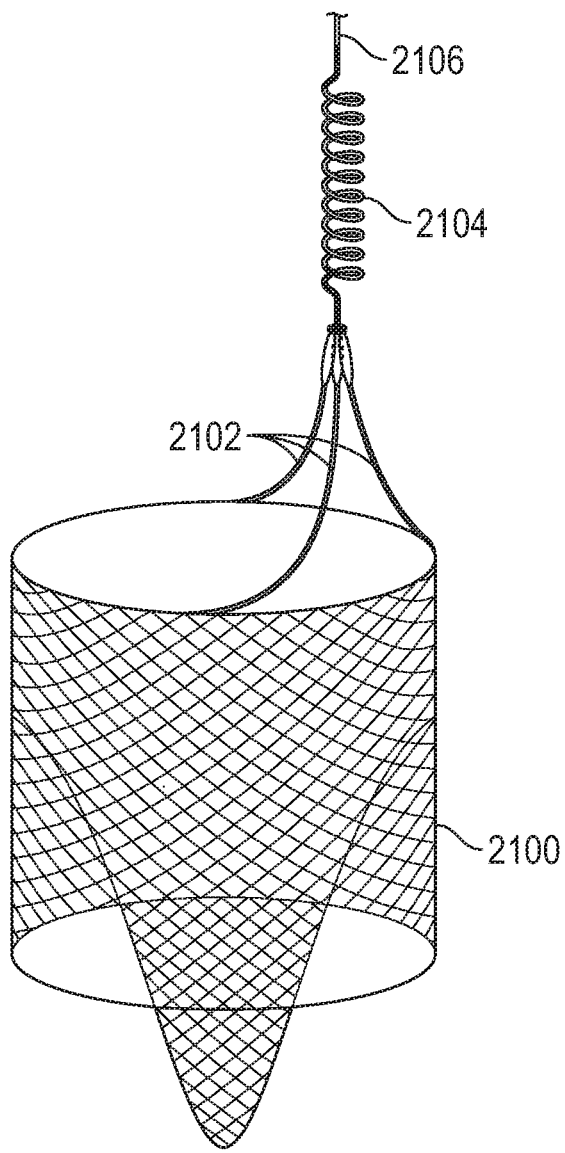
FIG. 21A shows a peripheral vascular filter according to some aspects.

FIG. 21A shows a peripheral vascular filter according to some aspects. The filter includes a primary filter 2100. The filter further includes a plurality of retractor wires 2102. The filter may include three retractor wires 2102, as shown in FIG. 21A, or it may include more or fewer retractor wires. The filter includes a spring system 2104. The spring system 2104 can include a coil spring that can expand and contract. The length of the spring when maximally stretched may be equal to 150%-200% the length of the spring when no stretching forces are applied. The spring system is positioned to prevent pushing and pulling filter when forces are applied to the filter wire 2106. The spring system plus the self-expanding filter body create an added anchoring force that provides stability for the filter. When forces are applied to the filter wire 2106, the spring system can expand or contract to absorb the tension, and prevent the forces from dislodging the filter from its position in the tissue cavity.

Figure 21B:
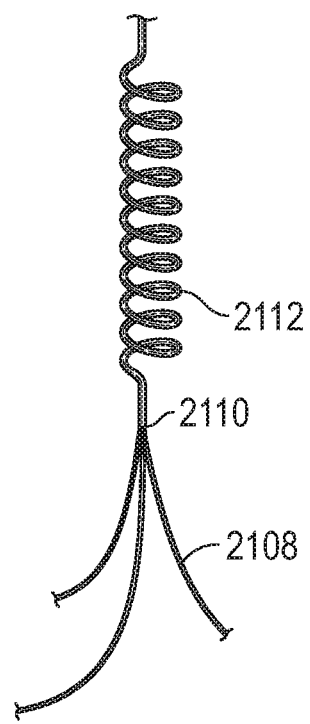
FIG. 21B shows the spring system of FIG. 21A.

FIG. 21B shows the spring system of FIG. 21A. According to one aspect, the retractor wires 2108 each have a diameter of about 0.11 inches, the three grouped retractor wires 2110 have a diameter of about 0.33 inches, and the spring 2112 has a diameter of about 0.35 inches. In one aspect, the spring system has a maximum diameter that is less than 0.4 inches. In one aspect, the spring system has maximum diameter that is within 10% of the combined diameter of the retractor wires. These dimensions are exemplary and non-limiting, and other dimensions may be used.

Figure 21C:
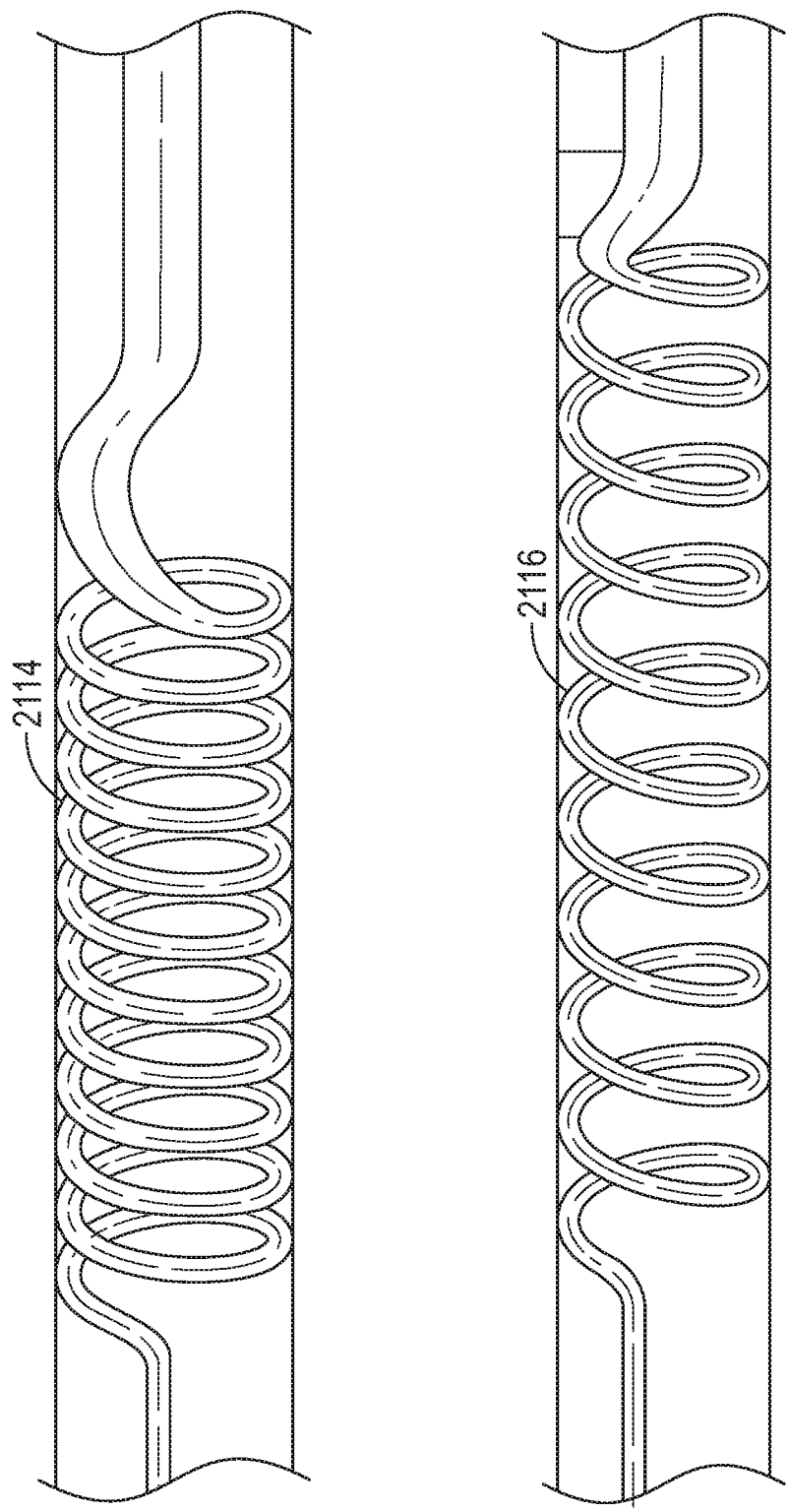
FIG. 21C shows the spring system in two configurations.

FIG. 21C shows the spring system in a first configuration 2114 when the spring system is pre-loaded and not stretch, and in a second configuration 2216 when the spring system is pre-loaded and stretched.

Figure 22A:
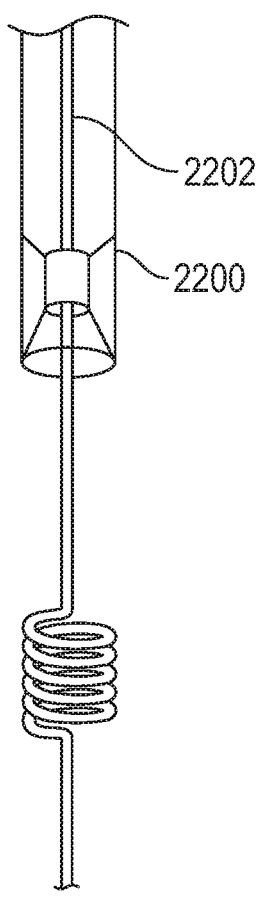
FIG. 22A shows additional aspects of the retrieval of the filter.
Figure 22B:
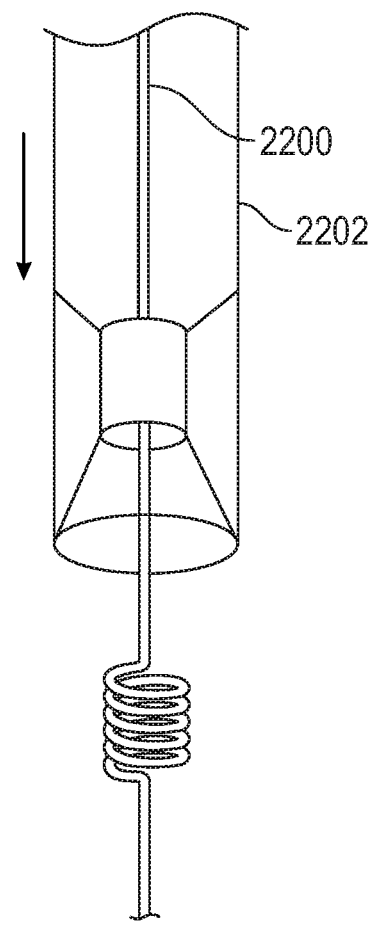
FIG. 22B shows additional aspects of the retrieval of the filter.
Figure 22C:
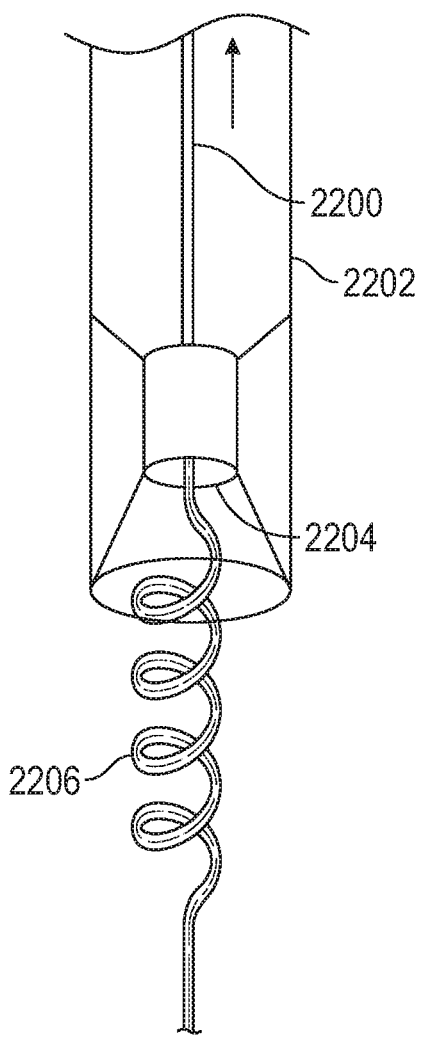
FIG. 22C shows additional aspects of the retrieval of the filter.
Figure 22D:
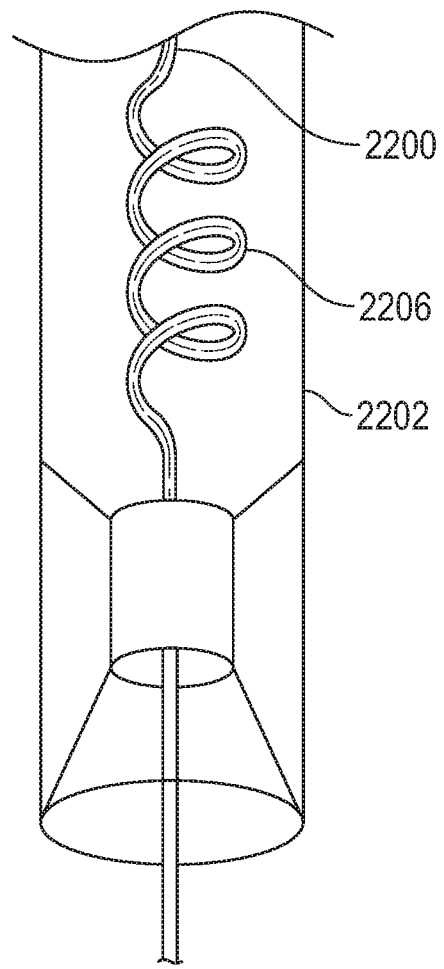
FIG. 22D shows additional aspects of the retrieval of the filter.

FIGS. 22A-22F show additional aspects of the retrieval of the filter. First, an operator advances the retrieval catheter 2200 over the filter spring wire 2202, as shown in FIG. 22A. Then, the operator initiates pulling of the filter wire 2202 (also referred to as a "filter spring wire" or a "guide wire") into the retrieval catheter 2200 while slowly advancing the retrieval catheter 2200. This is shown in FIG. 22B. As shown in FIG. 22C, the filter spring wire 2202 is pulled into the retrieval catheter 2200 through a narrow lumen 2204 until the entire spring 2206 is beyond the retrieval catheter tip. FIG. 22D shows the spring 2206 in the retrieval catheter 2200.

Figure 22E:
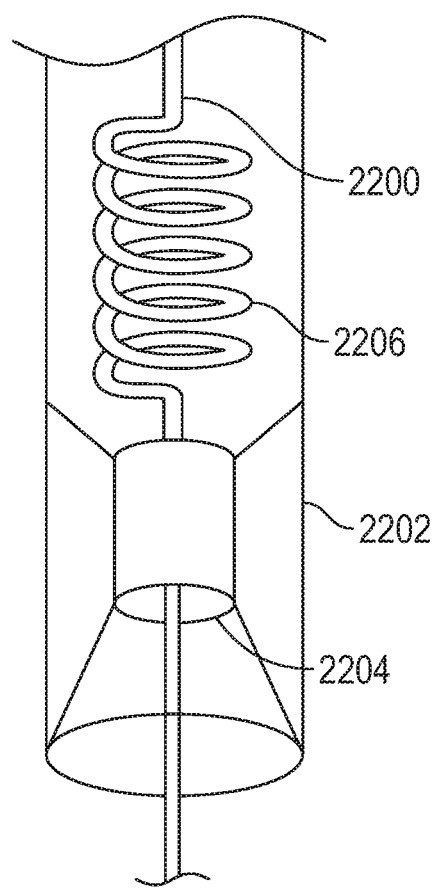
FIG. 22E shows additional aspects of the retrieval of the filter.
Figure 22F:
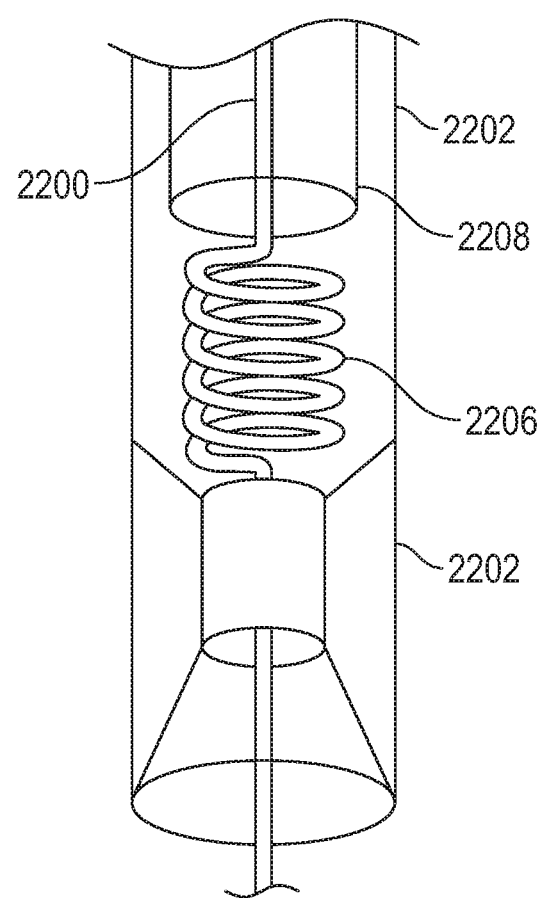
FIG. 22F shows additional aspects of the retrieval of the filter.

As shown in FIG. 22E, once the spring 2206 has gone through the narrow catheter lumen 2204, the spring 2206 is allowed to return to a non-stretched spring configuration. The narrow catheter lumen 2204 acts as a stopper for the spring 2206 from falling out of the retrieval catheter. Then, as shown in FIG. 22F, the operator can advance a filter spring wire condenser 2208 inside the retrieval catheter 2200 over the filter spring wire 2202. The filter spring wire condenser 2208 prevents the spring 2206 from stretching during the additional pull back on the filter spring wire 2202 and this strengthens the filter spring wire 2202 for the final stages of retrieval.

Figure 23E:
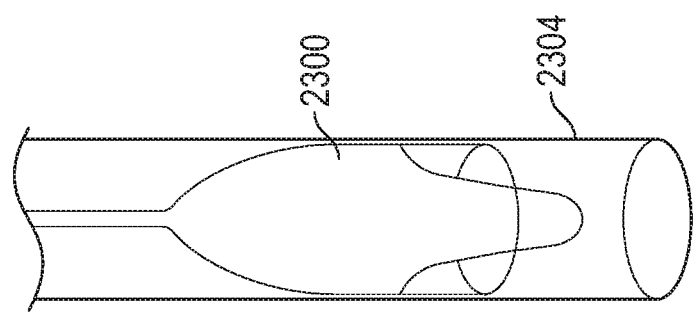
FIG. 23E shows a final stage of retrieval of the filter into the retrieval catheter.
Figure 23D:
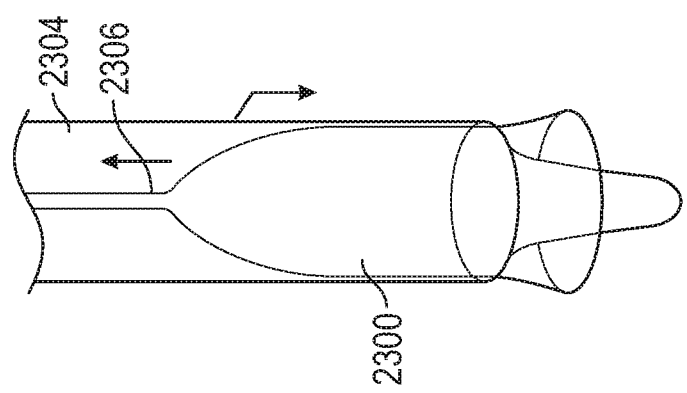
FIG. 23D shows an additional stage of retrieval of the filter into the retrieval catheter.
Figure 23C:
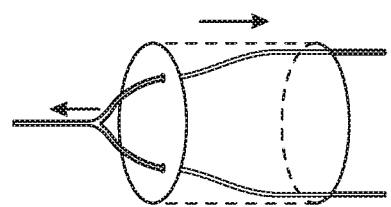
FIG. 23C shows an additional stage of retrieval of the filter into the retrieval catheter.
Figure 23B:
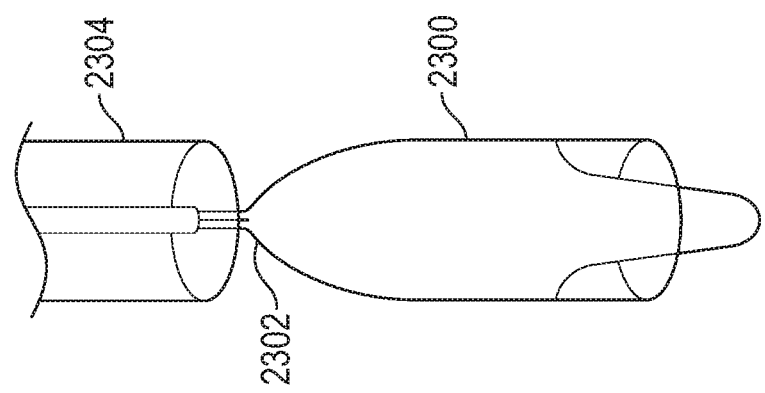
FIG. 23B shows an additional stage of retrieval of the filter into the retrieval catheter.
Figure 23A:
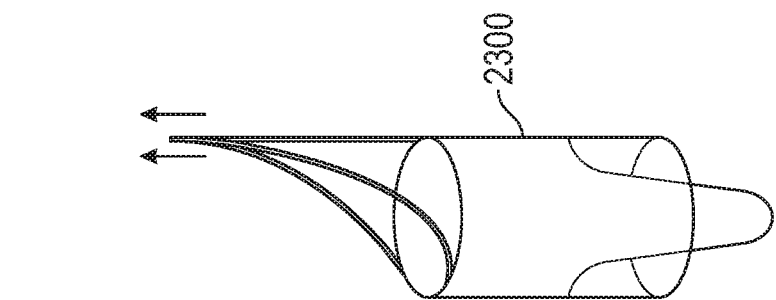
FIG. 23A shows a stage of retrieval of the filter into the retrieval catheter.

FIG. 23A-23E show the final stages of retrieval. FIG. 23A shows the initiation of a pulling force on the filter 2300. The force is generated by the filter spring wire condenser which is housed inside the retrieval catheter. The filter spring wire condenser may also be referred to as a spring wire retrieval catheter. As shown in FIG. 23B, the filter 2300 is pulled by the spring wire retrieval catheter, causing the filter's proximal portion 2302 to collapse and enter the retrieval catheter 2304. FIG. 23C shows two forces resulting from two action performed at the same time. The upwards arrow indicate the pulling force from the spring wire retrieval catheter. The downward arrow indicates the downward pushing force from the retrieval catheter.

FIG. 23D shows the filter 2300 mostly disposed inside the retrieval catheter 2304. The filter 2300 shows important configuration changes including closure of the orifice at the proximal end 2306 of the filter 2300. FIG. 23E shows the filter 2300 retrieved into the retrieval catheter 2304, which complete the filter retrieval process.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. Moreover, features described in connection with one embodiment of the invention may be used in conjunction with other embodiments, even if not explicitly stated above. It is therefore to be understood that, within the scope of the claims and their equivalents, the invention may be practiced otherwise than as specifically described.

I claim:

1. A peripheral vascular filter comprising:
   a filter body forming a cavity therein, the filter body having an opening in a proximal end thereof;
   a catheter adapted to form a helix concentric to the filter body, a distal end of the catheter being fixed to the filter body and a proximal end of the catheter extending proximal to the filter body;
   a plurality of expandable filter walls connected to the filter body adjacent to the opening;
   a plurality of retractor wires, each retractor wire having a distal end connected to one of the plurality of expandable filter walls, and a proximal end connected to the catheter proximal to the filter body,
   wherein, in a deployed configuration, the plurality of expandable filter walls are compressed, and the opening in the proximal end of the filter body is unobstructed, and in a retrieval configuration, the expandable filter walls are expanded to obstruct the opening in the proximal end of the filter body, and
   wherein the expandable filter walls are expanded by a force applied to the proximal end of the catheter.

2. The peripheral vascular filter of claim 1, wherein the filter body comprises a stent forming the opening in a proximal end thereof, and a cone-shaped filter connected to the stem to close a distal opening of the stent.

3. The peripheral vascular filter according to claim 2, wherein the filter body further includes a support ring at a distal end of the stem.

4. The peripheral vascular filter according to claim 2, wherein the stent is a self-expanding stent.

5. The peripheral vascular filter according to claim 1, further comprising a guide wire disposed inside the catheter.

6. The peripheral vascular filter according to claim 5, wherein the guide wire comprises at least one spring portion, the at least one spring portion adapted to absorb forces exerted on the guide wire to prevent the peripheral vascular filter from becoming dislodged.

7. The peripheral vascular filter according to claim 1, further comprising a spring wire system, the spring wire system adapted to absorb forces exerted on the peripheral vascular filter to prevent the peripheral vascular filter from becoming dislodged.

8. The peripheral vascular filter according to claim 7, wherein the spring wire system comprises a helical spring and a solid core wire.

9. The peripheral vascular filter according to claim 1, wherein the filter body comprises a porous material having pores between about 10 μm and about 80 μm.

10. The peripheral vascular filter according to claim 9, wherein the pores of the filter body are larger at the proximal end of the filter body than at a distal end of the filter body.

11. The peripheral vascular filter according to claim 1, wherein the filter body further includes a support ring at the proximal end of the filter body.

12. The peripheral vascular filter according to claim 1, wherein, in the deployed configuration, the filter body exerts an expansion force on a tissue lumen in which the filter body is disposed, creating a friction force that resists displacement of the filter body in the tissue lumen.

13. The peripheral vascular filter according to claim 1, wherein the filter body comprises a cylindrical primary filter and a cone-shaped secondary filter attached to the primary filter.

14. The peripheral vascular filter according to claim 13, wherein the secondary filter is partially disposed inside a lumen formed by the primary filter.

15. The peripheral vascular filter according to claim 13, wherein a proximal end of the secondary filter is connected to an inner surface of the primary filter.

16. The peripheral vascular filter according to claim 1, wherein the peripheral vascular filter is adapted for use in a peripheral vasculature.

17. The peripheral vascular filter according to claim 1, wherein the plurality of retractor wires comprises three retractor wires.

\* \* \* \* \*